United States Patent
Young et al.

(10) Patent No.: US 7,393,531 B2
(45) Date of Patent: *Jul. 1, 2008

(54) CYTOTOXICITY MEDIATION OF CELLS EVIDENCING SURFACE EXPRESSION OF MCSP

(75) Inventors: David S. F. Young, Toronto (CA); Susan E. Hahn, Toronto (CA); Helen P. Findlay, Toronto (CA); Alison L. Ferry, Toronto (CA)

(73) Assignee: Arius Research Inc., Toronto, Ontario (CA)

( * ) Notice: Subject to any disclaimer, the term of this patent is extended or adjusted under 35 U.S.C. 154(b) by 352 days.

This patent is subject to a terminal disclaimer.

(21) Appl. No.: 10/810,744

(22) Filed: Mar. 26, 2004

(65) Prior Publication Data
US 2004/0197328 A1   Oct. 7, 2004

Related U.S. Application Data

(63) Continuation-in-part of application No. 10/762,129, filed on Jan. 20, 2004, which is a continuation-in-part of application No. 10/743,451, filed on Dec. 19, 2003, now abandoned, which is a continuation of application No. 10/348,231, filed on Jan. 21, 2003, now Pat. No. 7,009,040.

(51) Int. Cl.
*A61K 39/395* (2006.01)
*A61K 39/00* (2006.01)
*C07K 16/00* (2006.01)
*C12P 21/08* (2006.01)

(52) U.S. Cl. .............. 424/141.1; 424/155.1; 424/181.1; 424/183.1; 424/133.1; 530/388.1; 530/388.8; 530/391.1; 530/391.7

(58) Field of Classification Search .............. 424/141.1; 530/388.1
See application file for complete search history.

(56) References Cited

U.S. PATENT DOCUMENTS

| | | | |
|---|---|---|---|
| 4,861,581 A | 8/1989 | Epstein et al. |
| 4,879,225 A | 11/1989 | Morgan et al. |
| 5,017,693 A | 5/1991 | Hylarides et al. |
| 5,034,223 A | 7/1991 | Abrams et al. |
| 5,112,954 A | 5/1992 | Abrams et al. |
| 5,171,665 A | 12/1992 | Hellstrom et al. |
| 5,270,202 A | 12/1993 | Raychaudhuri |
| 5,484,596 A | 1/1996 | Hanna, Jr. et al. |
| 5,493,009 A | 2/1996 | Ferrone |
| 5,580,774 A | 12/1996 | Beavers et al. |
| 5,693,763 A | 12/1997 | Codington et al. |
| 5,707,603 A | 1/1998 | Toner et al. |
| 5,750,102 A | 5/1998 | Eisenbach et al. |
| 5,780,029 A | 7/1998 | Ferrone |
| 5,780,033 A | 7/1998 | Torchilin et al. |
| 5,783,186 A | 7/1998 | Arakawa et al. |
| 5,817,774 A | 10/1998 | Delecki et al. |
| 5,849,876 A | 12/1998 | Linsley et al. |
| 5,869,045 A | 2/1999 | Hellstrom et al. |
| 5,869,268 A | 2/1999 | Kudo et al. |
| 6,180,357 B1 | 1/2001 | Young et al. |
| 6,238,667 B1 | 5/2001 | Kohler |
| 6,248,870 B1 | 6/2001 | Delecki et al. |
| 2004/0141913 A1 | 7/2004 | Young et al. |

FOREIGN PATENT DOCUMENTS

| | | |
|---|---|---|
| EP | 380607 | 12/1994 |
| WO | WO92/16646 | 10/1992 |
| WO | WO 03/086456 | 10/2003 |

OTHER PUBLICATIONS

Taber's Cyclopedic Medical Dictionary (1985, F.A. Davis Company, Philadelphia, p. 274).*
Busken, C et al, (Digestive Disease Week Abstracts and Itinerary Planner, 2003, abstract No. 850).*
Krontiris and Capizzi (Internal Medicine, 4th Edition, Editor-in-chief Jay Stein, Elsevier Science, 1994 Chapters 71-72, pp. 699-729).*
Carter, S. K. et al. Chemotherapy of Cancer; Second edition; John Wiley & Sons: New York, 1981; appendix C.*
Gura (Science, 1997, 278:1041-1042).*
Winter et al (TIPS, 1993, 14:139-143).*
Baselga et al (J. Clin. Oncol, 1996, 14:737-744).*
Kimball (Introduction to Immunology, 3rd ed. Macmillan, Inc, New York, 1990, p. 507).*
Miller and Tannock (The Basic Science of Oncology, 2nd ed., McGraw- Hill Inc., 1992, Ch.14).*

(Continued)

*Primary Examiner*—Susan Ungar
*Assistant Examiner*—Peter J. Reddig
(74) *Attorney, Agent, or Firm*—McHale & Slavin, P.A.

(57) ABSTRACT

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays which utilize the CDMABs of the instant invention.

10 Claims, 11 Drawing Sheets

OTHER PUBLICATIONS

Riechmann et al (Nature vol. 332:323-327 1988).*
T. Karpanen et al, "Vascular endothelial growth factor C promotes tumor lymphangiogenesis and intralymphatic tumor growth", Cancer Research, 61:1786-1790 (Mar. 2001).
W. Waud et al, "Characterization of in vivo mammary and prostate tumor xenograft models for growth and response to clinical anticancer agents", Contrib Oncol Basel Karger, 54:305-315 (1999).
G. Klement et al, "Differences in therapeutic indexes of combination metronomic chemotherapy and an anti-VEGFR-2 antibody in multidrug-resistant human breast cancer xenografts", Clinical Cancer Research, 8:221-232 (Jan. 2002).
D. Blakey et al, "Antitumor activity of the novel vascular targeting agent ZD6126 in a panel of tumor models", Clinical Cancer Research, 8:1974-1983 (Jun. 2002).
Z. Xiao et al, "Generation of a baculovirus recombinant prostate-specific membrane antigen and its use in the development of a novel protein biochip quantitative immunoassay", Protein Expression and Purification, 19:12-21 (2000).
S. Guichard et al, "Schedule-dependent activity of topotecan in OVCAR-3 ovarian carcinoma xenograft: pharmacokinetic and pharmacodynamic evaluation", Clinical Cancer Research, 7:3222-3228 (Oct. 2001).
V. Von Gruenigen et al, "Efficacy of intraperitoneal adenovirus-mediated p53 gene therapy in ovarian cancer", Int. J. Gynecol. Cancer, 9:365-372 (1999).
N. Guilbaud et al, "Marked antitumor activity of a new potent acronycine derivative in orthotopic models of human solid tumors", Clinical Cancer Research, 7:2573-2580 (Aug. 2001).
K. Olson et al, "Inhibition of prostate carcinoma establishment and metastatic growth in mice by an antiangiogenin monoclonal antibody", Int. J. Cancer, 98:923-929 (2002).
S. Hirschfeld et al, "Oncology drug development: United States Food and Drug Administration perspective", Critical Reviews in Oncology/Hematology, 42:137-143 (2002).
P. Therasse et al, "New guidelines to evaluate the response to treatment in solid tumors", Journal of the National Cancer Institute, 92(3):205-216 (Feb. 2000).
G. Eckhardt et al, "Developmental therapeutics: successes and failures of clinical trial designs of targeted compounds", in American Society of Clinical Oncology, pp. 209-219 (2003).
P. Smith et al, "Anti-interleukin-6 monoclonal antibody induces regression of human prostate cancer xenografts in nude mice", The Prostate, 48:47-53 (2001).
T. Bumol et al, "Unique glycoprotein-proteoglycan complex defined by monoclonal antibody on human melanoma cells", Proc. Natl. Acad. Sci. USA, 79(4):1245-1249 (Feb. 1982).
P. Chattopadhyay et al, "Murine monoclonal anti-idiotope antibody breaks unresponsiveness and induces a specific antibody response to human melanoma-associated proteoglycan antigen in cynomolgus monkeys", Proc. Natl. Acad. Sci. USA, 89:2684-2688 (Apr. 1992).
T. Bumol et al, "Monoclonal antibody and an antibody-toxin conjugate to a cell surface proteoglycan of melanoma cells suppress in vivo tumor growth", Proc. Natl. Acad. Sci. USA, 80(2):529-533 (Jan. 1983).
G. Pluschke et al, "Molecular cloning of a human melanoma-associated chondroitin sulfate proteoglycan", Proc. Natl. Acad. Sci. USA, 93:9710-9715 (Sep. 1996).
J. Iida et al, "Melanoma chondroitin sulfate proteoglycan regulates matrix metalloproteinase-dependent human melanoma invasion into type I collagen", J. Biol. Chem., 276(22):18786-18794 (Jun. 2001).
K. Eisenmann et al, "Melanoma chondroitin sulphate proteoglycan regulates cell spreading through Cdc42, Ack-1 and p130cas", Nature Cell Biology, 1:507-513 (Dec. 1999).
S. Ferrone et al, "Human high molecular weight-melanoma associated antigen mimicry by mouse antri-idiotypic monoclonal antibodies MK2-23 experimental studies and clinical trials in patients with malignant melanoma", Pharmac. Ther., 57:259-290 (1993).
A. Mittelman et al, "Human high molecular weight melanoma-associated antigen (HMW-MAA) mimicry by mouse anti-idiotypic monoclonal antibody MK2-23: induction of humoral anti-HMW-MAA immunity and prolongation of survival in patients with stage IV melanoma", Proc. Natl. Acad. Sci. USA, 89:466-470 (Jan. 1992).
H. Ming Yang et al, "Doxorubicin conjugated with a monoclonal antibody directed to a human melanoma-associated proteoglycan suppresses the growth of established tumor xenografts in nude mice", Proc. Natl. Acad. Sci. USA, 85:1189-1193 (Feb. 1988).
M. Kusama et al, "Characterization of syngeneic antiidiotypic monoclonal antibodies to murine anti-human high molecular weight melanoma-associated antigen monoclonal antibodies", J. Immunol., 143(11):3844-3852 (Dec. 1989).
T. Bumol et al, "Biosynthetic studies of proteoglycans in human melanoma cells with a monoclonal antibody to a core glycoprotein of chondroitin sulfate proteoglycans", J. Biol. Chem., 259(20):12733-12741 (Oct. 1984).
D. Demetrick et al, "ME491 melanoma-associated glycoprotein family: antigenic identity of ME491, NKI/C-3, neuroglandular antigen (NGA), and CD63 proteins", J. Natl Cancer Inst, 84(6):422-429 (Mar. 1992).
C. Vennegoor et al, "Circulating melanoma-associated antigen detected by monoclonal antibody NKI/C-3", Cancer Immunol Immunother, 23:93-100 (1986).
M. Wang et al, "An ocular melanoma-associated antigen", Arch Ophthalmol., 110:399-404 (Mar. 1992).
B. Ulbricht et al, "Influence of 12(S)-hydroxyeicosatetraenoic acid (12(S)-HETE) on the localization of cathepsin B and cathepsin L in human lung tumor cells", European Journal of Cell Biology, 74:294-301 (Nov. 1997).
J. Harper et al, "Inhibition of anchorage-independent growth of human melanoma cells by a monoclonal antibody to a chondroitin sulfate proteoglycan", JNCI, 71(2):259-263 (Aug. 1983).
R. Oldham et al, "Monoclonal antibody therapy of malignant melanoma: in vivo localization in cutaneous metastasis after intravenous administration", J. Clin Oncol, 2(11):1235-1244 (Nov. 1984).
K. Imai et al, "Higher cytolytic efficiency of an IgG2a than of an IgG1 monoclonal antibody reacting with the same (or spatially close) determinant on a human high-molecular-weight melanoma-associated antigen", Cellular Immunology, 72:239-247 (1982).
M. Matsui et al, "Suppression of human melanoma growth in nude mice injected with anti high-molecular-weight melanoma-associated antigen monoclonal antibody 225.28S conjugated to purothionin", Jpn. J. Cancer Res., 76:119-123 (Feb. 1985).
B. Wilson et al, "Distribution and molecular characterization of a cell-surface and a cytoplasmic antigen detectable in human melanoma cells with monoclonal antibodies", Int. J. Cancer, 28:293-300 (1981).
M. Schrappe et al, "Long-term growth suppression of human glioma xenografts by chemoimmunoconjugates of 4-desacetylvinblastine-3-carboxyhydrazide and monoclonal antibody 9.2.27", Cancer Research, 52:3838-3844 (Jul. 1992).
T. Ghose et al, "Regression of human melanoma xenografts in nude mice injected with methotrexate linked to monclonal antibody 225.28 to human high molecular weight-melanoma associated antigen", Cancer Immunol Immunother, 34:90-96 (1991).
N. Cascinelli et al, "Anti-melanoma monoclonal antibody 225-28S: evaluation of toxicity in man", Tumori, 74:35-40 (1988).
E. Neuwelt et al, "Increased delivery of tumor-specific monoclonal antibodies to brain after osmotic blod-brain barrier modification in patients with melanoma metastatic to the central nervous system", Neurosurgery, 20 (6):885-895 (Jun. 1987).
G. Goodman et al, "Pilot trial of murine monoclonal antibodies in patients with advanced melanoma". J. Clin Oncol, 3(3):340-352 (Mar. 1985).
R. Reisfeld, "Immunochemical characterization of human tumor antigens", Seminars in Oncology, 13(2):153-164 (Jun. 1986).
P. Garin-Chesa et al, "Cell surface molecules of human melanoma immunohistochemical analysis of the gp57, GD3, and mel-CSPG antigenic systems", American Journal of Pathology, 134(2):295-303 (Feb. 1989).
H. Jacques Garrigues et al, "The melanoma proteoglycan: restricted expression on microspikes, a specific microdomain of the cell surface", J. Cell Biol., 103:1699-1710 (Nov. 1986).
F. Real et al, "Surface antigens of melanomas and melanocytes defined by mouse monoclonal antibodies: specificity analysis and comparison of antigen expression in cultured cells and tissues", Cancer Research, 45:4401-4411 (Sep. 1985).

W. Rettig et al, "Human melanoma proteoglycan: expression in hybrids controlled by intrinsic and extrinsic signals", Science, 231:1281-1284 (Mar. 1986).

Z. Jian Chen et al, "Modulation by adjuvants and carriers of the immunogenicity in xenogeneic hosts of mouse anti-idiotypic monoclonal antibody MK2-23, an internal image of human high molecular weight-melanoma associated antigen", Cancer Research, 53:112-119 (Jan. 1993).

R. Reisfeld et al, "Human tumor-associated antigens defined by monoclonal antibodies", CRC Critical Reviews in Immunology, 5(1):27-53.

I. Hellstrom et al, "Studies of a high molecular weight human melanoma-associated antigen", J. Immunol., 130(3):1467-1472 (Mar. 1983).

A. Mittelman et al, "Active specific immunotherapy in patients with melanoma", J. Clin. Invest., 86:2136-2144 (Dec. 1990).

P. Chattopadhyay et al, "Human high molecular weight-melanoma associated antigen mimicry by an anti-idiotypic antibody: characterization of the immunogenicity and the immune response to the mouse monoclonal antibody IMel-1", Cancer Research, 51:6045-6051 (Nov. 1991).

K. Imai et al, "Selective in vitro toxicity of purothionin conjugated to the monoclonal antibody 225.28S to a human high-molecular-weight melanoma-associated antigen", Cancer Immunol Immunother, 15:206-209 (1983).

K. Imai et al, "Monoclonal-antibodies to human melanoma-associated antigens", Transplantation Proceedings, 12(3):380-383 (Sep. 1980).

A. Mittelman et al, "Human high molecular weight-melanoma associated antigen mimicry by mouse anti-idiotypic monoclonal antibody MK2-23: modulation of the immunogenicity in patients with malignant melanoma", Clinical Cancer Research, 1:705-713 (Jul. 1995).

M. Saleh et al, "Immunologic response to the dual murine anti-Id vaccine melimmune-1 and melimmune-2 in patients with high-risk melanoma without evidence of systemic disease", J. Immunother., 21(5):379-388 (1998).

P. Chattopadhyay et al, "Monoclonal anti-idiotypic antibodies to human melanoma-associated proteoglycan antigen: generation and characterization of anti-idiotype antibodies", Cancer Research, 51:3183-3192 (Jun. 1991).

W. Quan et al, "Active specific immunotherapy of metastatic melanoma with an antiidiotype vaccine: a phase I/II trial of I-Mel-2 plus SAF-m", J. Clin Oncol., 15(5):2103-2110 (May 1997).

\* cited by examiner

A.

B.

CYTOTOXICITY MEDIATION OF CELLS EVIDENCING SURFACE EXPRESSION OF MCSP

REFERENCE TO RELATED APPLICATIONS

This application is a continuation-in-part of application Ser. No. 10/762,129, filed Jan. 20, 2004, which is a continuation-in-part of application Ser. No. 10/743,451, filed Dec. 19, 2003, now abandoned, which is a continuation of application Ser. No. 10/348,231, filed Jan. 21, 2003, now U.S. Pat. No. 7,009,040, issued on Mar. 7, 2006, the contents of each of which are herein incorporated by reference.

FIELD OF THE INVENTION

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays, which utilize the CDMAB of the instant invention.

BACKGROUND OF THE INVENTION

Melanoma-associated chondroitin sulfate proteoglycan (MCSP) was identified independently by several investigators who developed monoclonal antibodies to human metastatic melanoma cell lines. Several antibodies were found to react with a specific antigen associated with the melanoma cell surface. The independent development of these antibodies led to the multiplicity of names for the target antigen, all of which were subsequently determined to be MCSP. MCSP has therefore also been referred to as high molecular weight melanoma associated antigen (HMW-MAA), human melanoma proteoglycan (HMP), melanoma-associated proteoglycan antigen (MPG) and melanoma chondroitin sulfate proteoglycan (mel-CSPG), and has been identified as the antigen of various specific antibodies, some of which have been set out below. MCSP was also found to be over 80 percent homologous with the rat proteoglycan NG2 and is hence also referred to by that name.

MCSP is a glycoprotein-proteoglycan complex consisting of an N-linked glycoprotein of 250 kDa and a proteoglycan component >450 kDa. The core glycoprotein is present on the surface of melanoma cells, either as a free glycoprotein or modified by the addition of chondroitin sulfate. The molecular cloning of MCSP led to the identification of several structural features. There are 3 extracellular domains containing a total of 10 cysteines (5 potential disulfide bridges), 15 possible N-linked glycosylation sites, and 11 potential chondroitin sulfate attachment sites. The transmembrane segment has a single cysteine, however the functional significance of that residue has not been established. The cytoplasmic domain has 3 threonine residues that may serve as sites for phosphorylation by protein kinase C, although it has not yet been shown that MCSP is phosphorylated.

It has been shown that MCSP is expressed in the majority of melanoma cancers, and it was originally thought that it had a very limited distribution on normal cells and other tumor types. One early study that led to this conclusion used immunohistochemistry (IHC) on normal and tumor tissues fixed with formaldehyde or methanol in order to determine the distribution of MCSP using anti-MCSP antibody B5. In this study, antibody B5 was found to react with 17 out of 22 melanoma tumors tested, 2 out of 2 astrocytomas tested, and none of the 23 carcinomas tested. Out of 22 normal tissues tested, B5 was found to bind only skin keratinocytes, lung alveolar epithelium and capillary endothelium.

Another study examined the tissue distribution of MSCP as defined by anti-MCSP antibody 9.2.27 using frozen tissue sections. Again, reactivity was found in all melanoma tissues and cell lines tested, but there was no reactivity in any of the 6 various carcinoma tumors tested. Out of the 7 fetal tissues tested, reactivity was only observed in the skin and faintly in the aorta while in adult tissues, reactivity was only seen in 3 out of 13 tissues tested.

A subsequent study examined the distribution of MCSP using the anti-MCSP antibodies B5, 9.2.27, 225.28S and A0122, all of which recognize distinct epitopes of MCSP. This study was performed on frozen tissues. It was found that all of the anti-MCSP antibodies had similar staining patterns, reacting with normal and malignant tumors of neural, mesenchymal and epithelial origin, that were previously thought to be MCSP negative. Specifically, the antibody B5 reacted with various epithelial, connective, neural and muscular tissues in the 24 organs that were tested, and reacted with 28 out of 34 various tumors tested. The authors explained that the differences between their findings and previous reports were due to the use of improved and more consistent IHC techniques, noting that choice of fixative was important, presumably leading to the conclusion that an important characteristic of the MCSP antigen is its sensitivity to the processing steps involved in IHC.

A further study was carried out in order to localize MCSP at the ultrastructural level. Immunolocalization studies using electron microscopy demonstrated that MSCP was localized almost exclusively to microspikes, a microdomain of the melanoma cell surface that may play a role in cell-cell contact and cell-substratum adhesion.

The molecular cloning of MCSP in 1996 enabled northern blot analysis of MCSP expression in tumor cell lines and normal human tissues using MCSP cDNA probes. Out of 8 various tumor cell lines tested, expression of MCSP was observed only in the melanoma cell line. MCSP expression was not seen in any of the 16 normal adult and 4 normal fetal tissues tested. The discrepancies found in different studies of tissue localization of MCSP indicate that further study may be required to elucidate the actual expression patterns of this antigen or to account for the differences that have been reported.

Since proteoglycans have been known to mediate cell-cell and cell-extracellular matrix (ECM) interactions, the role of MCSP in these processes has been investigated. MCSP has been shown to stimulate $\alpha_4\beta_1$-integrin mediated adhesion and spreading of melanoma cells, and it has also been proposed that signaling through the MCSP core protein induces recruitment and tyrosine phosphorylation of $p130^{cas}$ which may regulate cell adhesion and motility, contributing to tumor invasion and metastasis. The combination of these results indicated that MCSP may function to enhance adhesion of melanoma cells by both activating integrins and stimulating pathways that lead to cytoskeletal rearrangement.

MCSP has also been found to associate with membrane-type 3 matrix metalloproteinase (MT3-MMP), likely through the chondroitin sulfate component of MCSP. It has been suggested that MT3-MMP expression in melanomas in vivo could promote the degradation of ECM proteins in the vicinity of the growing tumor, providing space in which the tumor can expand. Therefore, the association between MT3-MMP and MCSP may be an activation step to promote melanoma invasion.

Several in vitro assays using anti-MCSP antibodies have been carried out to examine the role of MCSP in processes linked to tumor invasion and metastasis. The role of MCSP in anchorage-independent growth was assessed using the antibody 9.2.27. Melanoma cells cultured in soft agar containing 9.2.27 showed a 67-74 percent specific decrease in their colony formation. These findings suggested that MCSP might be involved in cell-cell interaction, and contribute to anchorage-independent growth. The same authors also examined the effects of blocking MCSP with 9.2.27 in assays measuring the adhesion of M14 melanoma cells on basement membranes of bovine aorta endothelial (BAE) cells. The effect of 9.2.27 treatment was compared to treatment with a control monoclonal antibody W6/32 (directed against all class I histocompatibility antigens). M14 control cells and M14 cells pretreated with antibody were plated on basement membranes of BAE cells. A significant inhibition of 27 percent in cell adhesion was observed in 9.2.27 treated cells, whereas no significant effect was observed in W6/32 treated cells. A more striking effect of cell pretreatment with 9.2.27 was the inhibition of cell spreading which was verified at the ultrastructural level using scanning electron microscopy.

Many of the antibodies that were developed against melanoma cells and determined to specifically recognize MCSP have been tested in both in vitro and in vivo assays to determine their anti-cancer effects.

Monoclonal antibody 9.2.27 recognizes the core glycoprotein component of MCSP and was one of the first antibodies investigated for tumor suppressing properties. Bumol et al. investigated 9.2.27 and a diphtheria toxin A (DTA) conjugate of 9.2.27 for immunotherapy of melanoma tumors grown in nude mice. In vitro cytotoxicity assays were first carried out by measuring the effects of both 9.2.27 and 9.2.27-DTA conjugate on protein synthesis in M21 human melanoma cells as indicated by protein incorporation of [$^{35}$S]methionine. The 9.2.27-DTA conjugate significantly inhibited protein synthesis in M21 melanoma cells, though a greater effect was seen with unconjugated DTA. There was only minimal effect achieved by 9.2.27 alone. Both the 9.2.27 and 9.2.27-DTA conjugate were investigated for anti-tumor effects in human melanoma tumor-bearing nude mice. M21 tumor mince was implanted subcutaneously and allowed to establish growth for 3 days, then mice were treated at day 3 and at 3 day intervals thereafter with either 9.2.27 or 9.2.27-DTA conjugate. Tumor volumes of treated mice were compared to those of untreated control mice. At day 18 (the last day for which data was reported), 9.2.27 treated mice showed a 64 percent inhibition of tumor growth while 9.2.27-DTA conjugate treated mice showed a 52 percent inhibition of tumor growth, compared to untreated controls. In this initial study the authors concluded that 9.2.27 and 9.2.27-DTA conjugate were approximately equivalent in their effect on suppression of growth of M21 melanoma tumors in nude mice. While this initial study reports in vivo suppression of tumor growth by treatment with 9.2.27, several subsequent studies, including those by the same authors, have demonstrated that naked 9.2.27 did not exhibit any anti-tumor effects in vivo. Collectively, as outlined below, the experiments carried out to investigate the utility of using 9.2.27 to treat human tumors have demonstrated that, although cancer cells were targeted by 9.2.27, no anti-cancer activity resulted from treatment with the naked antibody.

A phase I clinical trial was carried out which was designed to give large doses of 9.2.27 in anticipation of later therapeutic studies with 9.2.27 immunoconjugates. Eight patients with malignant melanoma whose tumors reacted with 9.2.27 by flow cytometry and/or immunoperoxidase staining, received single doses of antibody intravenously, twice weekly on a dose escalating scale of 1, 10, 50, 100 and 200 mg. Although none of the patients experienced significant toxicity and 9.2.27 localized to the metastatic melanoma nodules, no clinical responses were observed.

In a later study, 9.2.27 was conjugated to the chemotherapeutic drug doxorubicin (DXR), and the conjugate was investigated for growth inhibition of melanoma in vitro and in vivo. Growth inhibition of M21 cells treated with the DXR-9.2.27 conjugate was measured using a [$^3$H]thymidine incorporation assay. The conjugate showed specific dose-dependent growth inhibition of the M21 target cells and no effect on an MCSP negative control cell line. No in vitro assays were carried out examining effects of 9.2.27 alone. To investigate the DXR-9.2.27 conjugate in vivo, M21 cells were injected subcutaneously and allowed to establish a tumor for 8-10 days. Injections were given intravenously at day 10 and at 3 day intervals thereafter for 30 days. Significant suppression of tumor growth was seen only in mice treated with the DXR-9.2.27 conjugate. Both DXR treatment alone and 9.2.27 treatment alone failed to suppress tumor growth; a mixture of 9.2.27 and DXR showed similar negative effects.

Another study was carried out investigating the effects of a 9.2.27 conjugate. Schrappe et al. conjugated the chemotherapeutic agent 4-desacetylvinblastine-3-carboxyhydrazide (DAVLBHY) to 9.2.27 and tested its effect on human gliomas. Nude mice were injected with U87MG (a human glioma cell line) cells subcutaneously and the animals were treated on days 2, 5, 7, and 9. Tumor volume was most effectively reduced by the 9.2.27-DAVLBHY conjugate. Control groups, which were treated with either PBS or 9.2.27 alone, developed fast growing tumors and there was no reduction in tumor volume in 9.2.27 treated mice compared to mice treated with PBS.

Antibody 225.28S was made against the human M21 melanoma cell line, and was initially described as reacting with a high molecular weight melanoma associated antigen. This molecule was subsequently shown to be the same molecule as MCSP. An early study tested the cytolytic ability of 225.28S, an IgG$_{2a}$, on a human melanoma cell line and compared it to another anti-MCSP antibody, clone 653.40S that was an IgG$_1$. 225.28S and 653.40S were determined to recognize the same, or spatially close, antigenic determinants on MCSP. It was found that neither antibody could lyse melanoma cells in conjunction with complement in vitro assays. Both antibodies could mediate lysis of target melanoma cells in an antibody-dependent cell-mediated (ADCC) cytotoxicity assay, with 225.28S exhibiting a higher lytic activity than 653.40S. However, lysis of melanoma cells was only obtained with a significantly higher effector/target cell ratio than had been reported by others using anti-melanoma antigen antibodies. The authors concluded that the lack of cytolytic activity of these antibodies in conjunction with human complement and the high effector/target cell ratio required for lysis to occur in ADCC suggested that the injection of monoclonal antibodies into melanoma patients was not likely to cause the destruction of tumor cells. The authors suggested that the immunotherapeutic use of these antibodies should be limited to utilizing them as carriers of radioisotope, chemotherapeutic or toxic agents.

Naked antibody 225.28S was investigated for its therapeutic potential in a phase I trial where it was delivered intravenously in 10 mg doses to 2 patients with end-stage melanoma. Although no clinically adverse or major toxic effects were noted that could be ascribed to the administration of the antibody, there was also no positive therapeutic response.

Antibody 225.28S was conjugated to purothionin, a low molecular weight polypeptide that is especially toxic to dividing cells, and was tested for its in vitro toxicity to the human melanoma cell line Colo 38. It was found that the culture of Colo 38 cells with the 225.28S-purothionin conjugate for 24 hr inhibited $^3$H-thymidine uptake. In addition, the viability of Colo 38 cells was dramatically reduced in cultures incubated with the conjugate for 7 days. Although in vitro toxicity was observed, there was still a fraction of melanoma cells that survived the 225.28S-purothionin treatment. The authors suggested that the immunotherapy of malignant diseases may have to rely on cocktails of monoclonal antibodies to distinct tumor associated antigens as carriers of toxic agents, indicating that 225.8S conjugate alone would not be sufficient for treatment of cancer. The effect of 225.28S-purothionin conjugate treatment was evaluated on the growth of human melanoma in nude mice. Colo 38 cells were implanted either subcutaneously or intraperitoneally in nude mice. Treatments were made on days 1, 3 and 5 for the intraperitoneal implanted mice and on days 1, 3, 5 and 20 for the subcutaneous implanted mice. Survival was monitored for all mice. The only statistically significant prolongation of survival was observed in the intraperitoneal implanted mice that were treated with the 225.28S-purothionin conjugate. 225.28S alone, purothionin alone or a mixture of 225.28S and purothionin did not enhance survival in either the intraperitoneal or the subcutaneous implanted mice. Tumor volume was also recorded for the subcutaneous implanted mice and it was found that only the 225.28S-purothionin conjugate treatment significantly reduced tumor volume. Treatment with 225.28S alone did not result in a reduction of tumor volume.

225.28S was also conjugated to the chemotherapeutic drug methotrexate (MTX) and its effects on tumor growth were investigated in vivo. Nude mice were inoculated subcutaneously with M21 human melanoma cells and treated on days 1, 4, 7, 10 and 14. The MTX-225.28S conjugate was the only treatment that inhibited tumor growth. 225.28S alone, MTX alone or a mixture of 225.28S and MTX failed to inhibit tumor growth. 225.28S was used in a study designed to investigate the potential toxic effects in humans due to the administration of a reagent of a xenogenic nature. 85 patients with metastatic cutaneous melanoma were administered either intact 225.28S or the F(ab')$_2$ fragment that were labeled with $^{131}$I, $^{123}$I, $^{111}$In, or $^{99}$Tc. The amount of injected antibody ranged from 14 to 750 µg. No clinically detectable side effects were observed in any of the patients. No clinical response was reported, though it was not necessarily anticipated as this study was designed for toxologic purposes.

225.28S was used to generate murine anti-idiotypic monoclonal antibodies including the antibody MF11-30, which bears the mirror image of MCSP. MF11-30 has been shown to induce the development of anti-MCSP antibodies in both a syngeneic and xenogeneic system. MF11-30 was tested in 2 clinical trials in escalating doses designed to test the toxicity and response in patients with advanced malignant melanoma. In both studies there were few side effects due to administration of the antibody and the therapy was well tolerated. In the second trial the average survival of 7 patients who developed anti-anti-idiotypic antibodies with a titer of at least 1:8 and displayed no marked changes in the level of serum MCSP was 55 weeks (range 16-95), which was significantly higher than the remaining 12 patients (who developed anti-antiidiotypic antibodies with a titer of 1:4 or less and displayed an increase in the serum level of MCSP) whose average survival was 19 weeks (range 8-57).

Antibody 763.74 was also generated against melanoma cells and recognizes MCSP. There have not been any reports of in vitro or in vivo anti-cancer effects of antibody 763.74, however this antibody was also used to generate murine anti-idiotypic monoclonal antibodies. One of these antibodies, MK2-23, bears the internal image of the determinant defined by the anti-MCSP antibody 763.74. In preclinical experiments, immunization with MK2-23 was shown to induce the development of anti-MCSP antibodies in both a syngeneic host (BALB/c mice) and in a xenogenic host (rabbit). The immunogenicity of MK2-23 was markedly enhanced when it was conjugated to the carrier protein keyhole limpet hemocyanin (KLH) and administered with an adjuvant. A clinical trial was carried out to characterize the humoral response induced by MK2-23 in patients with melanoma. 25 patients with stage IV melanoma were immunized on days 0, 7 and 28 with 2 mg subcutaneous injections of MK2-23 conjugated to KLH and mixed with Bacillus Calmette Guerin (BCG). Additional injections were given if the titer of anti-anti-idiotypic antibodies was low. Approximately 60 percent of the patients who were immunized with MK2-23 developed anti-MCSP antibodies, although the level and affinity of the anti-MCSP antibodies were low. It was found that survival of patients who developed anti-MCSP antibodies after immunizaiton with MK2-23 was significantly longer than those who did not. The median survival of patients who developed anti-MCSP antibodies was 52 weeks (range 19-93) while the median survival of the 9 patients without detectable anti-MCSP antibodies in their sera was 19 weeks (range 9-45). Three patients who developed anti-MCSP antibodies experienced a partial remission of their disease. Although promising results were achieved in this study, 40 percent of the patients immunized with MK2-23 did not respond with detectable anti-MCSP antibodies. As well, the 3 patients who had achieved partial remission all eventually experienced recurrence of disease. An attempt was made to increase the immunogenicity of MK2-23 by pretreatment of patients with a low dose of cyclophosphamide (CTX), which had been reported to enhance the cellular and humoral response to tumor associated antigens by selectively inactivating some sets of suppressor cells. However, no effects of pretreatment with CTX on the immunogenicity of MK2-23 were detected.

Monoclonal antibody 48.7 was developed against the human metastatic melanoma cell line M1733 and was reported to react against a molecule subsequently determined to be MCSP. 48.7 was administered in a phase I clinical trial in combination with the murine monoclonal antibody 96.5, which is directed against the transferrin-like cell surface glycoprotein p97 that is present on human melanomas. Five patients received 2 mg each of mAbs 96.5 and 48.7 on day 1, 10 mg each on day 2, and 25 mg each on days 3 through 10. Treatment was well tolerated; however there were no clinical responses to treatment and disease progression occurred in all patients. These two antibodies were investigated in a separate clinical trial where 3 patients with melanoma metastatic to the central nervous system were treated with radiolabeled Fab fragments of either one of these antibodies. Two patients received 5 mg doses of $^{131}$I-labeled Fab fragment of 48.7 in conjunction with osmotic opening of the blood-brain barrier (BBB) in an effort to enhance entry of the antibody into tumors in the brain. The osmotic BBB modification increased the delivery of Fab to the tumor-bearing hemisphere and spinal fluid, but clear persistent localization of the antibody to the tumor was not shown. The authors hypothesized that the lack of localization may have been due to an inadequate dose of the antibody.

Melimmune was a dual preparation of two murine anti-idiotypic antibodies, Melimmune-1 (I-Mel-1) and Melimmune-2 (I-Mel-2), which mimic separate epitopes of MCSP. I-Mel-1 was a subclone of the anti-idiotypic antibody MF11-30, which was developed against the anti-MCSP antibody 225.28 (as previously discussed). I-Mel-1 was shown to induce an anti-MCSP response in rabbits. I-Mel-2 was an anti-idiotypic antibody developed against the anti-MCSP antibody MEM136, which reacts to a different epitope on MCSP than does 225.28. I-Mel-2 was also shown to induce an anti-MCSP response in rabbits. The Melimmune preparation, which contained a 1:1 composition of I-Mel-1 and I-Mel-2, was tested in a phase I trial of 21 patients with resected melanoma without evidence of metastatic disease. Detailed immune response analysis was reported for 12 of these patients enrolled in a single institution. Patients received Melimmune on 1 of 2 treatment schedules with doses that ranged from 0.2 to 4.0 mg (0.1 to 2.0 mg each of I-Mel-1 and I-Mel-2). All patients developed both anti-I-Mel-1 and anti-I-Mel-2 antibodies with the peak antibody response to I-Mel-2 greater than that to I-Mel-1 in 10 out of 12 patients.

However, this study was unable to demonstrate induction of specific antibodies to MCSP since none of the patient's sera was able to inhibit either binding of radiolabeled 225.28 to MCSP expressing Mel-21 cells, or binding of radiolabeled MEM136 to Mel-21 cells. A direct cell binding assay was also used to assay for the presence of anti-MCSP antibodies in patients sera; however, there was no difference in the binding of preimmune sera compared to postimmune sera to M21 cells in a FACS based assay.

I-Mel-2 was tested in a separate clinical trial where 26 patients with metastatic melanoma were treated with 2 mg I-Mel-2 and either 100 or 250 μg of the adjuvant SAF-m delivered intramuscularly biweekly for 4 weeks and then bimonthly until disease progression. Anti-MCSP antibodies were detected in 5 of the 26 patients using an inhibition radioimmunoassay. Of the 5 patients with detectable anti-MCSP antibodies, 1 patient experienced a complete remission, 1 had stable disease and the other 3 had progressive disease. The patient with complete remission had the highest titer of anti-MCSP antibodies (1:1500).

Prior Patents:

U.S. Pat. No. 5,270,202 (and its related patents: WO9216646A1, EP0576570A1) teaches an anti-idiotypic antibody, IMelpg2 (also known as "IM32") to MEM136, an antibody directed to human melanoma-associated proteoglycan (also known as "HMW-MAA"). The IMelpg2 antibody was shown to be directed to MEM136 specifically, and suggested to be of use for the diagnosis and treatment of disease in which cells expressed the MPG epitope. Although there was an effect of IMelpg2 on tumor cell invasion, as determined by in vitro assays it was neither the most effective antibody tested, nor was there indications of in vivo anti-tumor effects despite showing an Ab3 response.

EP0380607B 1 teaches anti-idiotypic antibodies to the Mab 225.28 which has specificity for an undefined epitope of HMW-MAA. These antibodies are useful as active immunotherapy for melanoma. Both MF11-30 and IMelpg1, and polyclonal anti-idiotypic antibodies to 225.28 have been reported and evaluated in animal models with MF11-30 undergoing clinical trials in melanoma patients, although there was no supporting data. MF11-30 can induce 225.28 idiotypic antibodies. The IMelpg1 cell line was derived from treating the MF11-30 cell line with BM Cycline and testing for the absence of mycoplasma contamination. Although antibodies to IMelpg1 can be induced in rabbit sera, and be shown to bind to the Colo38 melanoma cell, there was no indication of tumorcidal activity, either in vitro or in vivo.

U.S. Pat. No. 4,879,225 teaches the production of antibodies from insoluble immune complexes. In this case rat anti-idiotypic antibodies to Mab 9.2.27, an antibody directed against the HMW-MAA, were generated by immoblizing 9.2.27 on protein A-Sepharose for use as an antigen. Antibodies to melanoma cells were produced using a variety of cell or cell lysate complexes conjugated to Sepharose. Murine monoclonal antibodies that bound to melanoma cells, but not normal T-cells or B-cells were compared to 9.2.27. Those that had similar properties to 9.2.27 were selected for further characterization: NR-ML-02, NR-ML-03, NR-ML-04, NR-ML-05, NR-ML-06. Each of these antibodies were positive in a sandwich ELISA assay using 9.2.27 as the capture antibody and solublized SK MEL-28 melanoma membranes as an antigen source. Further these antibodies were characterized as recognizing melanoma tumor cells, and also reacting with smooth muscle and endothelial cells. An additional 61 anti-proteoglycan antibodies were produced with 10 recognizing the same determinant as NR-ML-02/NR-ML-04, 3 antibodies recognized the same determinant as NR-ML-03 or NR-ML-05; 45 did not recognize the same epitope as determined by the 5 antibodies. In U.S. Pat. No. 5,084,396 these antibodies were radiolabelled and compared with 9.2.27 for tumor uptake in nude mice bearing melanoma xenografts. The tumor uptake was the greatest for NR-ML-05 and NR-ML-02, then 9.2.27, and then NR-ML-02. In neither of these inventions were there indications that these antibodies produced reduction in tumor burden of cancerous disease, nor enhanced survival of mammals having cancerous disease.

U.S. Pat. No. 5,034,223 teaches a method of enhancing delivery of conjugated antibodies to tissues bearing tumor-associated antigens by pretreating with a non-conjugated blocking antibody. Antibodies to HMW-MAA, 9.2.27 and NR-ML-05, were conjugated to technicium 99 (Tc-99) and were administered in the clinical setting after prior administration of unlabelled Mab NR-2AD, an antibody with an anti-idiotype specific for only 1 patient's B-cell lymphoma. Since these studies were designed using Tc-99 as a reporter radioisotope, which does not have cytotoxic, or radioablative effects there was no evidence of anti-tumor effects although there was enhanced uptake of the anti-HMW-MAA antibodies through the use of this process.

U.S. Pat. No. 5,580,774 teaches the construction of a chimeric antibody using the antibody genes that encode Mab 9.2.27. No disclosures regarding the diagnosis or treatment of cancerous disease using the chimeric antibody were made.

U.S. Pat. No. 5,493,009 and U.S. Pat. No. 5,780,029 teaches the murine anti-idiotypic antibody MK2-23, and its conjugates, directed against an anti-HMW-MAA antibody, 763.74. MK2-23 can bind directly to 763.74 and inhibit 763.74 binding to Colo 38 melanoma cells. Further, Ab3 elicited by MK2-23 can directly bind HMW-MAA and can competitively inhibit 763.74 binding to Colo 38 melanoma cells. Active immunotherapy was carried out in a clinical trial in stage IV melanoma patients with MK2-23. In 89 percent of patient's post-immunization sera reacted with Colo 38 melanoma cells, and inhibited binding of 763.74 to Colo 38 cells suggesting induction of Ab3 antibodies. In 6 of 15 patients there was a reduction in size of metastatic lesions reported but study details were not furnished. The specificity of the antibodies in patient sera was partially characterized and it is unclear whether Ab3 antibodies, to the extent that they were present, were responsible for any of the clinical response observed, since the 763.74 antibody did not have innate anti-tumor effects. U.S. Pat. No. 5,866,124 teaches the chimeric anti-idiotypic antibody MK2-CHγ1, and its derivatives, directed against an anti-HMW-MAA antibody, 763.74, derived from MK2-23.

A number of inventions, such as U.S. Pat. No. 5,017,693, U.S. Pat. No. 5,707,603, U.S. Pat. No. 5,817,774, U.S. Pat. No. 6,248,870, U.S. Pat. No. 5,112,954, U.S. Pat. No. 6,238,667, teach conjugating compounds to antibodies directed against HMW-MAA but fail to disclose their utility in treatment of cancerous disease. Importantly, were these antibodies effective as anti-cancer therapies alone, they would not require a conjugate to impart either cytotoxic or cytostastic effects.

These patents and patent applications identify MCSP antigens and related antibodies but fail to disclose the isolated monoclonal antibody of the instant invention, or the utility of the isolated monoclonal antibody of the instant invention.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies, which are useful in treating a cancerous disease. For the purpose of this document, the terms "antibody" and "monoclonal antibody" (mAb) may be used interchangeably and refer to intact immunoglobulins produced by hybridomas (e.g. murine or human), immunoconjugates and, as appropriate, immunoglobulin fragments and recombinant proteins derived from said immunoglobulins, such as chimeric and humanized immunoglobulins, F(ab') and F(ab')$_2$ fragments, single-chain antibodies, recombinant immunoglobulin variable regions (Fv)s, fusion proteins etc. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming antibody conjugates.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies and/or a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

Using substantially the process of U.S. Pat. No. 6,180,357, and as disclosed in Ser. No. 10/348,231, the mouse monoclonal antibody 11BD-2E11-2 was obtained following immunization of mice with cells from a patient's breast tumor biopsy. The 11BD-2E11-2 antigen was expressed on the cell surface of several human cell lines from different tissue origins. The breast cancer cell line MCF-7 and ovarian cancer cell line OVCAR-3 were susceptible to the cytotoxic effects of 11BD-2E11-2 in vitro.

The result of 11BD-2E11-2 cytotoxicity against MCF-7 and OVCAR-3 cells in culture was further extended by its anti-tumor activity towards these cancer cells when transplanted into mice (as disclosed in Ser. No. 10/762,129). Preclinical xenograft tumor models are considered valid predictors of therapeutic efficacy.

In a preventative in vivo model of human breast cancer, 11BD-2E11-2 prevented tumor growth and reduced tumor burden (as disclosed in Ser. No. 10/762,129). At day 51 (soon after last treatment), the mean tumor volume in the 11BD-2E11-2 treated group was 20 percent of the isotype control. Monitoring continued past 280 days post-treatment. 40 percent of the 11BD-2E11-2 treatment group was still alive at over 7.5 months post-implantation. Conversely, the isotype control group had 100 percent mortality after 6.5 months post-treatment. Therefore 11BD-2E11-2 enhanced survival and decreased the tumor burden compared to the control-treated groups in a well-established model of human breast cancer.

To determine if 11BD-2E11-2 was efficacious in more than one model of human breast cancer, its anti-tumor activity against MDA-MB-468 (MB-468) cells in an established model of breast cancer was determined. 11BD-2E11-2 reduced tumor growth by 25 percent in comparison to the buffer control. Therefore, 11BD-2E11-2 was effective in preventing tumor growth in an established as well as a preventative breast cancer xenograft model. In addition, 11BD-2E11-2 displayed anti-tumor activity in at least two different models of breast cancer.

In addition to the beneficial effects in a model of human breast cancer, 11BD-2E11-2 treatment also had anti-tumor activity against OVCAR-3 cells in a preventative ovarian cancer model (as disclosed in Ser. No. 10/762,129). In this model, body weight was used a surrogate measure of tumor progression. At day 80 post-implantation (16 days after the end of treatment) the mice in the treated group had 87.6 percent the mean body weight of the control group (p=0.015). Thus, 11BD-2E11-2 treatment was efficacious as it delayed tumor progression compared to the buffer control treated group in a well-established model of human ovarian cancer. The anti-tumor activities of 11BD-2E11-2, in several different cancer models, make it an attractive anti-cancer therapeutic agent.

To determine if 11BD-2E11-2 was efficacious in more than one model of human ovarian cancer, its anti-tumor activity against ES-2+SEAP cells (ES-2 ovarian cancer cells transfected with human placental secreted alkaline phosphatase (SEAP)) in an established model of ovarian cancer was determined. 11BD-2E11-2 enhanced survival in a cohort of mice in the treatment group in comparison to buffer control. In addition, 1 mouse within the 11BD-2E11-2 treatment group displayed greatly reduced circulating SEAP levels after treatment. Circulating SEAP levels can be used as an indicator of tumor burden. Therefore, 11BD-2E11-2 was effective in preventing tumor growth in an established as well as a preventative ovarian cancer xenograft model. In addition, 11BD-2E11-2 displayed anti-tumor activity in two different models of human ovarian cancer.

In order to validate the 11BD-2E11-2 epitope as a drug target, the expression of 11BD-2E11-2 antigen in frozen normal human tissues was determined. By IHC staining with 11BD-2E11-2, the majority of the tissues failed to express the 11BD-2E11-2 antigen, including the cells of the vital organs, such as the liver, kidney and heart. Albeit, there was staining to the smooth muscle fibers of blood vessels in almost all of the tissues. There was also epithelial staining for some of the tissues.

Localization of the 11BD-2E11-2 antigen and its prevalence within breast cancer patients is important in assessing the benefits of 11BD-2E11-2 immunotherapy to patients and designing effective clinical trials. To address 11BD-2E11-2 antigen expression in breast tumors from cancer patients, tumor tissue samples from 8 (7 additional samples were completely detached or not representative of the tumor on the microarray slide) individual breast cancer patients were screened for expression of the 11BD-2E11-2 antigen. The results of the study showed that 62 percent of tissue samples positively stained for the 11BD-2E11-2 antigen. Expression of 11BD-2E11-2 within patient samples appeared specific for cancer cells as staining was restricted to malignant cells. In addition, 11BD-2E11-2 stained 0 of 3 (2 additional samples again were completely detached from the microarray slide) samples of normal tissue from breast cancer patients. When tumors were analyzed based on their stage, or degree to which the cancer advanced, results did not suggest a trend towards greater positive expression with higher tumor stage for 11BD-2E11-2. However, the result was limited by the small sample size.

As outlined herein, additional biochemical data also indicate that the antigen recognized by 11BD-2E11-2 is MCSP. This was supported by studies showing that 11BD-2E11-2 immunoprecipitated protein was recognized by an antibody to the rat homologue of MCSP, and that anti-MCSP immunoprecipitated protein was recognized by 11BD-2E11-2. These IHC and biochemical results demonstrate that 11BD-2E11-2 bound to the MSCP antigen. Thus, the preponderance of evidence showed that 11BD-2E11-2 mediated anti-cancer effects through ligation of an unique epitope present on MCSP.

In toto, this data demonstrates that the 11BD-2E11-2 antigen is a cancer associated antigen and is expressed in humans, and is a pathologically relevant cancer target. Further, this data also demonstrates the binding of the 11BD-2E11-2 antibody to human cancer tissues, and can be used appropriately for assays that can be diagnostic, predictive of therapy, or prognostic. In addition, the cell localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

A number of distinct anti-MCSP antibodies have been developed and tested in many in vitro and in vivo systems. In pre-clinical models, with the exception of one study that was not reproduced, naked anti-MCSP antibodies have been shown to be ineffective in tumor reduction or enhancement of survival in several different melanoma models and one glioma model; other cancer types have not been studied with anti-MCSP antibodies. All trials of naked anti-MCSP antibodies in humans have failed to result in any positive clinical outcomes. Naked 11BD-2E11-2 has been shown to enhance survival and decrease tumor burden in murine models of human breast cancer. 11BD-2E11-2 has also inhibited tumor progression and enhanced survival in murine models of human ovarian cancer. Anti-MCSP antibodies have been conjugated to numerous toxic or chemotherapeutic agents, and these conjugates have demonstrated positive in vivo results when tested in murine models of melanoma. There have been no reports of anti-MCSP conjugates tested in humans, so the safety of these conjugates is not known. Delivery of monoclonal antibody alone however has been well tolerated with little, if any associated toxicity. Therefore if treatment of a cancer patient with a naked anti-MCSP antibody could result in a positive clinical outcome, it would be beneficial and an improvement upon what is currently available. Conjugation to a toxic agent is not required for 11BD-2E11-2 to exhibit anti-cancer activity; therefore the specific safety concerns associated with administration of antibody-toxin conjugate are not applicable. Many anti-MCSP antibodies have also been used to generate anti-idiotypic antibodies, which have been tested in both animals and humans. In small non-blinded trials, when the immunization of patients with anti-idiotypic antibodies resulted in a detectable anti-MCSP immune response, there was an increase in median survival of these patients compared to patients who did not develop a specific immune response. In the examples given, targeting MCSP to obtain a positive clinical response may result through the administration of anti-idiotypic antibodies. A problem with this approach is that not all patients who were immunized with the anti-idiotypic antibodies developed an anti-MCSP response. Therefore if an anti-MCSP antibody were available that could result in positive clinical outcomes upon direct administration, this would overcome the problem of relying on a patient's own immune response for producing a clinical benefit. 11BD-2E11-2 is such an antibody as it directly targets MCSP and exhibits anti-cancer effects in pre-clinical xenograft tumor models, which are considered valid predictors of therapeutic efficacy.

In all, this invention teaches the use of the 11BD-2E11-2 antigen as a target for a therapeutic agent, that when administered can reduce the tumor burden (thereby delaying disease progression) of a cancer expressing the antigen in a mammal, and can also lead to a prolonged survival of the treated mammal. This invention also teaches the use of a CDMAB (11BD-2E11-2), and its derivatives, to target its antigen to reduce the tumor burden of a cancer expressing the antigen in a mammal, and to prolong the survival of a mammal bearing tumors that express this antigen. Furthermore, this invention also teaches the use of detecting the 11BD-2E11-2 antigen in cancerous cells that can be useful for the diagnosis, prediction of therapy, and prognosis of mammals bearing tumors that express this antigen.

If a patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibodies conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cell-mediated cytotoxicity (ADCC) or complement-dependent cytotoxicity (CDC). For example murine IgM and IgG2a antibodies can activate human complement by binding the C-1 component of the complement system thereby activating the classical pathway of complement activation which can lead to tumor lysis. For human antibodies, the most effective complement-activating antibodies are generally IgM and IgG 1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody-mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody-mediated cancer cell killing which are more widely accepted. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in preclinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach CDMAB and antigen binding fragments thereof.

It is a further objective of the instant invention to produce CDMAB whose cytotoxicity is mediated through ADCC.

It is yet an additional objective of the instant invention to produce CDMAB whose cytotoxicity is mediated through CDC.

It is still a further objective of the instant invention to produce CDMAB whose cytotoxicity is a function of their ability to catalyze hydrolysis of cellular chemical bonds.

A still further objective of the instant invention is to produce CDMAB which are useful in a binding assay for diagnosis, prognosis, and monitoring of cancer.

Other objects and advantages of this invention will become apparent from the following description wherein, by way of illustration and example, certain embodiments of this invention are set forth.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

EXAMPLE 1

Figure 1:
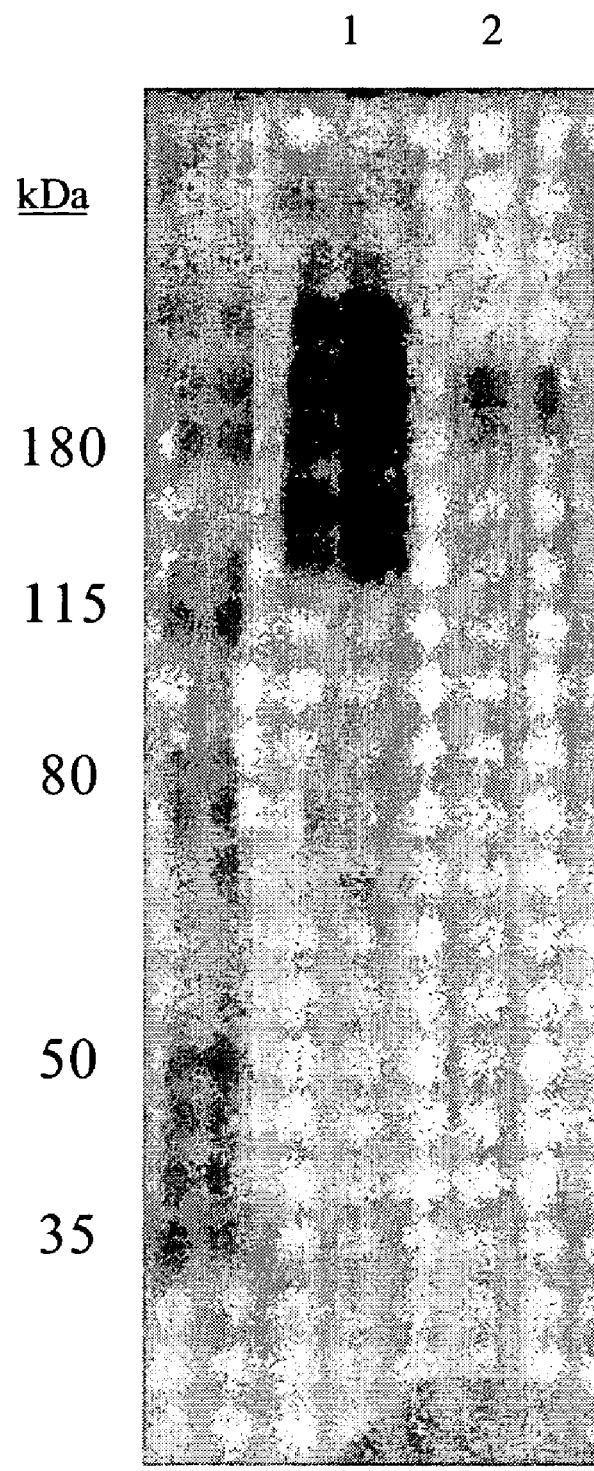
FIG. 1. Western blot of MDA-MB-231 (Lane 1) or OVCAR-3 (Lane 2) membranes probed with 11BD-2E11-2. Membrane proteins were separated under reducing conditions. Molecular weight markers are indicated on the right.

Identification of Binding Proteins by Western Blotting

To identify the antigen(s) recognized by the antibody 11BD-2E11-2, cell membranes expressing this antigen were subjected to gel electrophoresis and transferred using Western blotting to membranes to determine the proteins detected by this antibody.

1. Membrane Preparation

Previous work demonstrated binding by FACS of 11BD-2E11-2 to the breast cancer line MDA-MB-231 (MB-231). Previous work also demonstrated 11BD-2E11-2 efficacy against the ovarian cancer cell line OVCAR-3. Accordingly, membrane preparations from these 2 cell lines were used for antigen identification. Total cell membranes were prepared from confluent cultures of MB-231 breast cancer or OVCAR-3 ovarian cells. Media was removed from cell stacks and the cells were washed with phosphate buffered saline. Cells were dissociated with dissociation buffer (Gibco-BRL, Grand Island, N.Y.) for 20 min at 37° C. on a platform shaker. Cells were collected and centrifuged at 900 g for 10 min at 4° C. After centrifugation, cell pellets were resuspended in PBS and centrifuged again at 900 g for 10 min at 4° C. to wash. Pellets were stored at −80° C. Cell pellets were resuspended in homogenization buffer containing 1 tablet per 50 mL of Complete protease inhibitor cocktail (Roche, Laval QC) at a ratio of 3 mL buffer per gram of cells. The cell suspension was subjected to homogenization using a polytron homogenizer on ice in order to lyse the cells. The cell homogenate was centrifuged at 15,000 g for 10 min at 4° C. to remove the nuclear particulate. Supernatant was harvested, divided into tubes and then centrifuged at 75,600 g for 90 min at 4° C. Supernatant was carefully removed from the tubes and each membrane pellet was resuspended in approximately 5 mL homogenization buffer. The resuspended pellets from all tubes were combined in one tube and centrifuged at 75,600 g for 90 min at 4° C. Supernatant from the tubes was carefully removed, and the pellets were weighed. Solubilization buffer containing 1 percent Triton X-100 was added to the pellets at a ratio of 3 mL buffer per gram of membrane pellet. Membranes were solubilized by shaking on a platform shaker at 300 rpm for 1 hr on ice. The membrane solution was centrifuged at 75,600 g to pellet insoluble material. The supernatant containing the solubilized membrane proteins was carefully removed from tubes, assayed for protein content, and stored at −80° C.

2. SDS-PAGE and Western Blot

Membrane proteins were separated by SDS-polyacrylamide gel electrophoresis. 20 μg of membrane protein was mixed with SDS-PAGE sample buffer containing 100 mM DTT and was loaded onto a lane of an 8 percent SDS-PAGE gel. A sample of prestained molecular weight markers (Invitrogen, Burlington, ON) was run in a reference lane. Electrophoresis was carried out at 100 V for 10 minutes, followed by 150 V until sufficient resolution of the prestained molecular weight markers was observed. Proteins were transferred from the gel to PVDF membranes (Millipore, Billerica, Mass.) by electroblotting for 16 hr at 40 V. Transfer was assessed by noting complete transfer of the prestained markers from the gel to the membrane. Following transfer, membranes were blocked with 5 percent skim milk powder in Tris-buffered saline containing 0.5 percent Tween-20 (TBST) for 2 hr. Membranes were washed once with TBST and then incubated with 5 μg/mL 11BD-2E11-2 diluted in 3 percent skim milk powder in TBST for 2 hr. After washing 3 times with TBST, membranes were incubated with goat anti-mouse IgG (Fc) conjugated to horseradish peroxidase (HRP) from Jackson Immunologicals (West Grove Pa.). This incubation was followed by washing 3 times with TBST, followed by incubation with the HRP substrate 3,3',5,5'-tetramethyl benzidine (TMB) (substrate kit from Vector Laboratories, Burlington ON).

In FIG. 1 11BD-2E11-2 clearly binds to 3 molecular weight regions of the separated MB-231 (Lane 1) and OVCAR-3 (Lane 2) membrane proteins. By comparison to the molecular weight (MW) standards, the antibody binds to proteins of MW approximately 150, 240 and 280 kDa. All further studies were done using the MB-231 membranes since stronger reactivity was seen with this cell line.

EXAMPLE 2

Determining Glycosylation of Antigens Bound by 11BD-2E11-2

Figure 2:
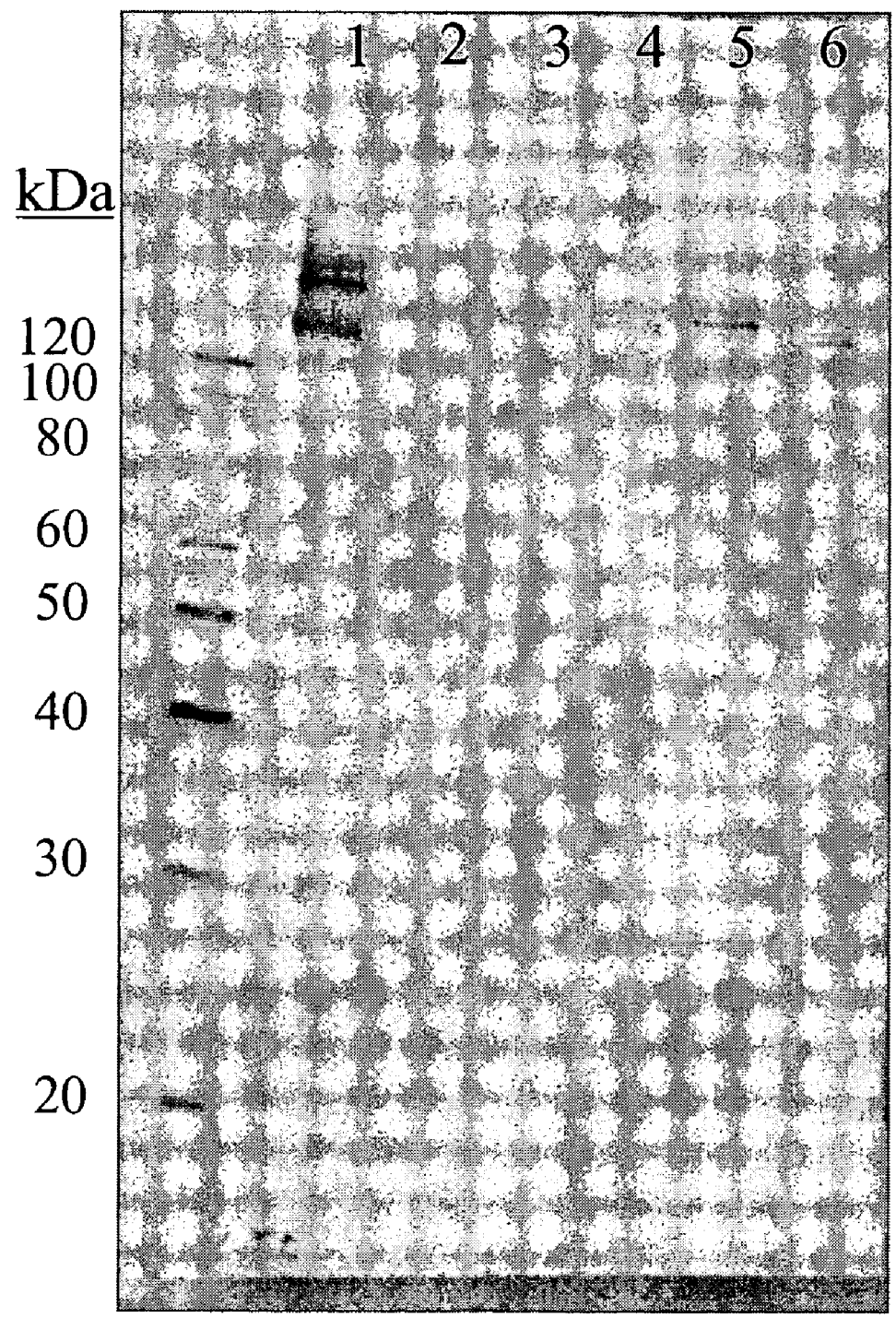
FIG. 2. Effect of deglycosylation on the binding of 11BD-2E11-2 to MDA-MB-231 membranes. 11BD-2E11-2 binding to MDA-MB-231 membranes that were incubated in deglycosylation buffer only (Lane 1), in a combination of PNGase F, endo-o-glycosidase, sialidase, galactosidase and glucosaminodase (Lane 2), in a combination of PNGase, endo-o-glycosidase and sialidase (Lane 3), in sialidase only (Lane 4), in endo-o-glycosidase only (Lane 5), and in PNGase only (Lane 6).

In order to determine if the antigen(s) recognized by the antibody 11BD-2E11-2 were glycoproteins, MB-231 membranes were incubated with different combinations of PNGase F, endo-o-glycosidase, sialidase, galactosidase and glucosaminidase. Membranes were separated by SDS-PAGE followed by Western blotting as described with 11BD-2E11-2. FIG. 2 demonstrates the result of 11BD-2E11-2 binding to MB-231 membranes that were incubated in deglycosylation buffer only (Lane 1), in a combination of PNGase F, endo-o-glycosidase, sialidase, galactosidase and glucosaminodase (Lane 2), in a combination of PNGase, endo-o-glycosidase and sialidase (Lane 3), in sialidase only (Lane 4), in endo-o-glycosidase only (Lane 5), and in PNGase only (Lane 6). Treatment of MB-231 membranes with glycosidases does not eliminate binding of 11BD-2E11-2, however a molecular weight shift of the proteins is observed in all lanes, indicating that the antigen recognized by 11BD-2E11-2 was a glycoprotein.

EXAMPLE 3

Identification of Antigens Bound by 11BD-2E11-2

1. Immunoprecipitation

The identification of the antigen for 11BD-2E11-2 was carried out by isolating the cognate ligand through immuno-precipitation of solublized membrane gylcoproteins with the antibody. 100 μL of Protein G Dynabeads (Dynal Biotech, Lake Success N.Y.) were washed 3 times with 1 mL of 0.1 M sodium phosphate buffer pH 6.0. 100 μg of 11BD-2E 11-2 in a total volume of 100 μL 0.1 M sodium phosphate buffer pH 6.0 was added to the washed beads. The mixture was incubated for 1 hr with rotational mixing. Unbound antibody was removed and the 11BD-2E11-2 coated beads were washed 3 times with 0.5 mL 0.1 M sodium phosphate pH 7.4 containing 0.1 percent Tween-20. The 11BD-2E11-2 coated beads were washed 2 times with 1 mL 0.2 M triethanolamine pH 8.2. 11BD-2E11-2 was chemically crosslinked to the beads by adding 1 mL of 0.02 M dimethylpimelimidate in 0.2 M triethanolamine pH 8.2 and incubating with rotational mixing for 30 min. The reaction was stopped by incubating the beads with 1 mL of 0.05 M Tris pH 7.5, for 15 min with rotational mixing. The 11BD-2E11-2 crosslinked beads were washed 3 times with 1 mL of 1 mM $KH_2PO_4$, 10 mM $Na_2HPO_4$, 137 mM NaCl, 2.7 mM KCl (PBS) containing 0.1 percent Tween-20. The 11BD-2E11-2 crosslinked beads were pre-eluted by incubation with 0.1 M citrate pH 3.0 for 3 min followed by 3 washes in 0.1 M PBS containing 0.1 percent Tween-20. A second set of antibody crosslinked beads were prepared in the same manner described using a mouse IgG, antibody (clone 107.3 from BD Biosciences, Oakville ON) to trinitrophenol, an irrelevant molecule, which was used as a negative IgG$_1$ isotype control.

The 11BD-2E11-2 crosslinked beads were blocked by incubating in 1 percent BSA in 0.1 M sodium phosphate pH 7.4 with rotational mixing for 30 minutes at 4° C. The beads were washed 3 times with 0.1 M sodium phosphate pH 7.4. 500 µg of total membrane preparation from MB-231 cells was incubated with the 11BD-2E11-2 crosslinked beads with rotational mixing for 2.5 hr at 4° C. The immunocomplex bound beads were washed three times with 1 mL of 1 mM KH$_2$PO$_4$, 10 mM Na$_2$HPO$_4$, 287 mM NaCl, 2.7 mM KCl containing 1 percent Triton X-100. 11BD-2E11-2 bound protein was eluted from the 11BD-2E11-2 crosslinked beads by incubation with 30 µL of 0.1 M citrate pH 3.0 for 3 min with gentle mixing. The eluted protein was brought to neutral pH by the addition of 9 µL of 1M Tris pH 9. The neutralized eluted protein was stored at −80° C. The 11BD-2E11-2 crosslinked beads were washed with 3 mL PBS containing 0.1 percent Tween-20. The IgG$_1$ isotype control (clone 107.3) crosslinked beads were incubated with MB-231 membrane proteins and processed in the same manner as the 11BD-2E11-2 beads.

Two batches of 11BD-2E11-2 immunoprecipitated protein from MB-231 membrane proteins were produced as described and combined together. The same was done for the IgG1 (clone 107.3) isotype control beads. Sixty-two percent of this immunoprecipitate mixture (corresponding to the amount of protein immunoprecipitated from 620 µg of MB-231 membrane proteins) was loaded onto a single lane of a 4-20 percent gradient SDS-PAGE gel. The same amount of material produced from the 107.3 crosslinked beads was loaded in an adjacent lane, as was 20 µg of MB-231 membrane proteins. A sample of unstained molecular weight markers (Invitrogen, Burlington ON) or pre-stained molecular weight markers were run in reference lanes. The sample was separated by electrophoresis at 100 V for 10 min, followed by 150 V for 60 minutes. Proteins were stained by incubating the gel in SYPRO Ruby™ (BioRad, Mississauga, ON). In a parallel Western blot, 18 percent of the immunoprecipitate mixture, which corresponded to the amount of protein immunoprecipitated from 180 µg of MB-231 membrane proteins, and the same amount of material produced from the IgG1 isotype control (clone 107.3) crosslinked beads, were separated by electrophoresis. Proteins were transferred from the gel to PVDF membranes (Millipore, Billerica, Mass.) by electroblotting for 16 hr at 40 V. After transfer, the membrane was blocked with 5 percent skim milk powder in TBST for 2 hr. The membrane was probed with 5 µg/mL 11BD-2E11-2 diluted in 3 percent skim milk powder in TBST for 2 hr. After washing 3 times with TBST, the membrane was incubated with goat anti-mouse IgG (Fc) conjugated HRP for 1 hr. This incubation was followed by washing 3 times with TBST, followed by incubation with the HRP substrate TMB.

Figure 3:
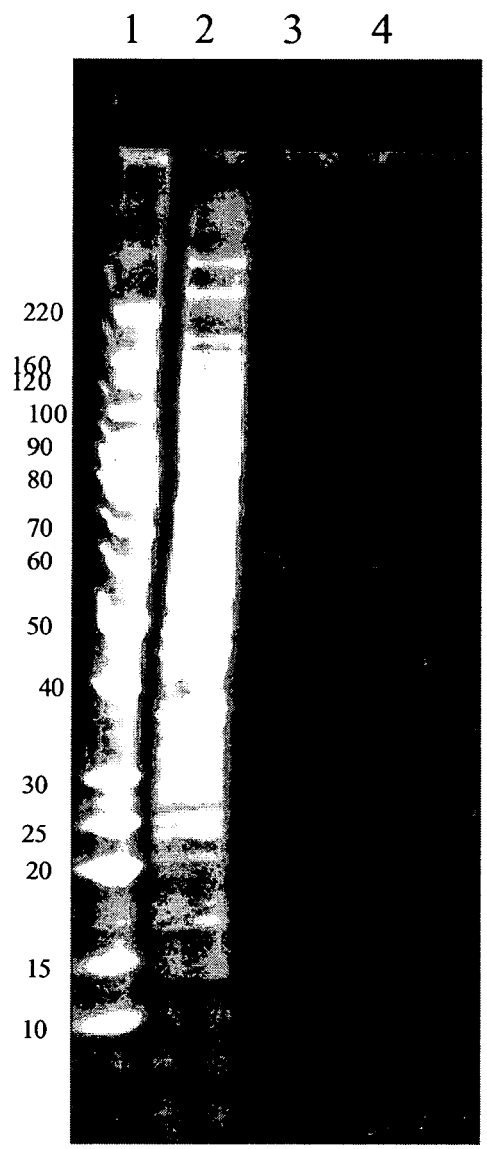
FIG. 3. SDS-PAGE (Panel A) and Western blot (Panel B) of MDA-MB-231 membrane proteins immunoprecipitated with 11BD-2E11-2. Lane 1 represents the molecular weight standard, Lane 2 the MDA-MB-231 membrane proteins, Lane 3 the 11BD-2E11-2 immunoprecipitated material and Lane 4 the isotype control immunoprecipitated material.
Figure 3:
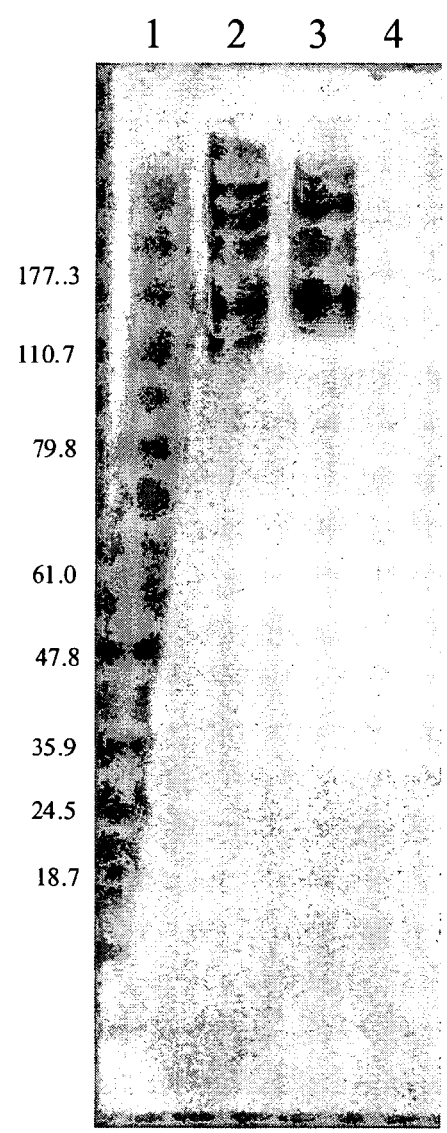

FIG. 3 depicts the gel and Western blot obtained from the proteins immunoprecipitated by 11BD-2E11-2. On the gel (Panel A) Lane 1 represents the molecular weight standard and Lane 2 represents the MB-231 membrane proteins. There were two distinct bands of MW 240 and 280 kDa in the lane containing the 11BD-2E11-2 immunoprecipitated material (Lane 3) that were not present in the lane containing the 107.3 immunoprecipitated material (Lane 4). On the corresponding Western blot (Panel B), 11BD-2E11-2 reacts strongly with the 11BD-2E11-2 immunoprecipitated proteins of MW 240 and 280 kDa (Lane 3). On the Western blot 11BD-2E11-2 also reacts strongly to an additional band in the 11BD-2E11-2 immunoprecipitated protein at 150 kDa; this band was not detectable on the stained gel. The reactivity profile of 11BD-2E11-2 to 11BD-2E 11-2 immunoprecipitated protein was similar to that seen in the MB-231 total membranes (Lane 2). There was no reactivity of 11BD-2E11-2 to proteins immunoprecipitated by IgG1 isotype control (clone 107.3; Lane 4), indicating that the binding of 11BD-2E11-2 to the immunoprecipitated protein was specific, and not due to the presence of contaminating proteins.

2. Mass Spectrometry

The regions of the gel corresponding to the 240 and 280 kDa protein immunoprecipitated by 11BD-2E11-2 (FIG. 3, Panel A, Lane 3) were cut out using sterile scalpels. These gel slices were then used for identification of proteins by mass spectrometry using MALDI/MS and LC/MS/MS.

The samples were subjected to proteolytic digestion on a ProGest workstation using trypsin, and a portion of the resulting digest supernatant was used for MALDI/MS analysis. Spotting was performed robotically (ProMS) with ZipTips; peptides were eluted form the C18 material with matrix (α-cyano 4-hydroxy cinnamic acid) prepared in 60 percent acetonitrile, 0.2 percent TFA. MALDI/MS data was acquired on an Voyager DE-STR instrument (Applied Biosystems, Foster City Calif. and the observed m/z values were submitted to ProFound (Proteometrics software package) for peptide mass fingerprint searching. ProFound queried a locally stored copy of the NCBInr database. An additional portion of the digest supernatant was analyzed by nano LC/MS/MS on a Micromass Q-Tof2 using a 75 µm C18 column at a flow-rate of 200 nL/min. MS/MS data were searched using a local copy of MASCOT.

The proteins identified by MALDI/MS and LC/MS/MS are presented in Table 1.

TABLE 1

Proteins Identified by 11BD-2E11-2 Immunoprecipitation of MDA-MB-231 Membranes

| Sample | Observed MW | Method | Protein ID | Percent coverage | # of peptides matched | NCBI accession # |
|---|---|---|---|---|---|---|
| A | 280 kDa | MALDI | Melanoma-associated chondroitin sulfate proteoglycan | 13 | 20 | gi 4503099 |
|   |   | LC/MS/MS | Melanoma chondroitin sulfate proteoglycan |   | 2 | gi 34148711 |
| B | 240 kDa | MALDI | Melanoma associated chondroitin sulfate proteoglycan | 14 | 21 | gi 4503099 |

Both samples were identified as melanoma-associated chondroitin sulfate proteoglycan (MCSP).

3. Confirmation

Figure 4:
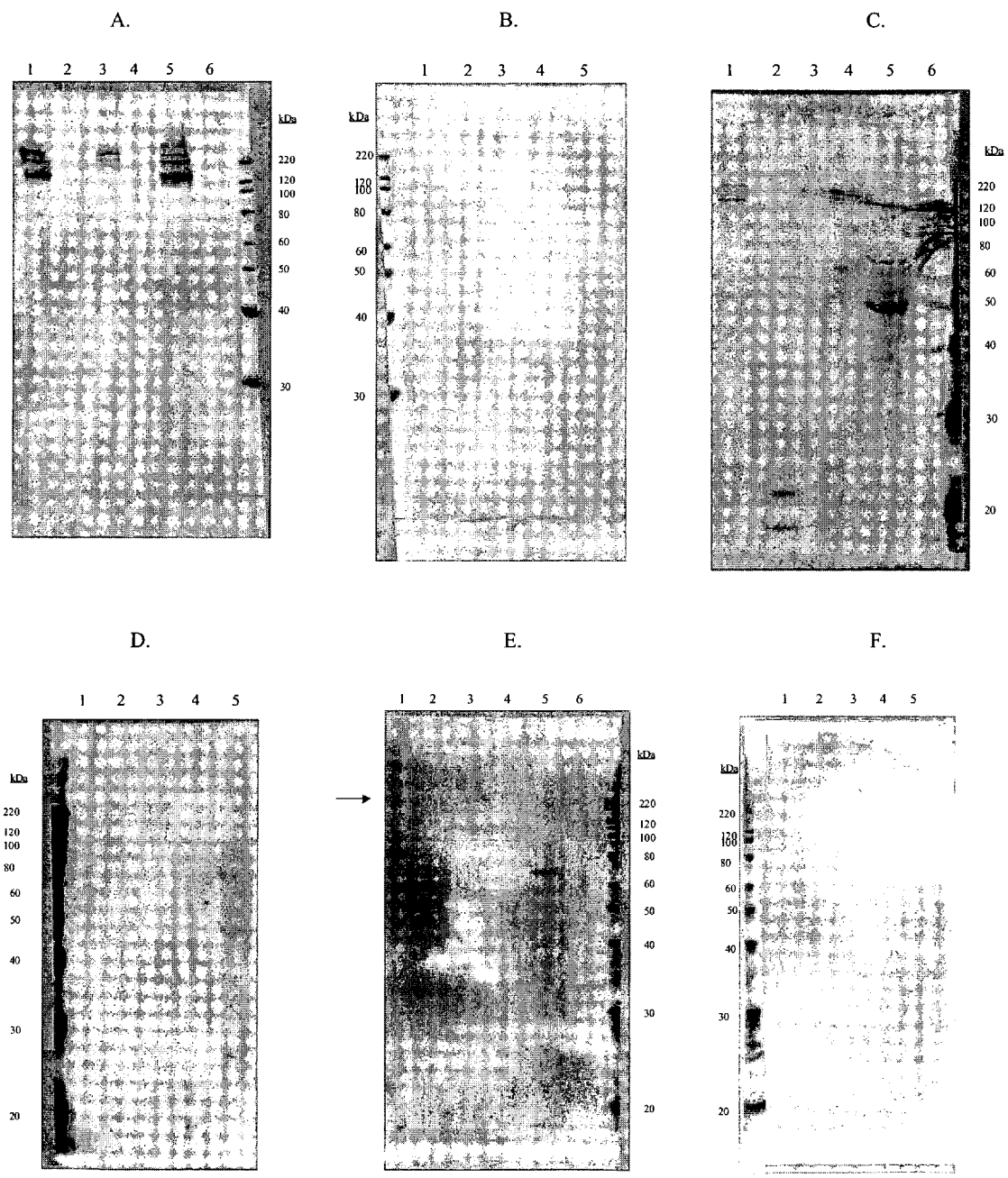
FIG. 4. Western blots of proteins probed with 11BD-2E11-2 (Panel A), IgG1 isotype control (clone 107.3, Panel B), anti-rat NG2 (polyclonal, Panel C), normal rabbit IgG (Panel D), anti-MCSP (clone 9.2.27, Panel E) and IgG2a isotype control (clone G155-228, Panel F). Lane 1: 11BD-2E 11-2 immunoprecipitate, Lane 2: IgG1 isotype control (clone 107.3) immunoprecipitate, Lane 3: anti-MCSP (clone 9.2.27) immunoprecipitate, Lane 4: IgG2a isotype control (clone G155-228) immunoprecipitate, Lane 5: MDA-MB-231 membranes and Lane 6: sample buffer only (negative control).

Confirmation of the putative antigen was carried out by determining whether known anti-MCSP antibodies would react with the protein immunoprecipitated by 11BD-2E11-2 and vice versa. Immunoprecipitates were prepared in the same manner as described previously except with the addition of the mouse anti-MCSP monoclonal antibody 9.2.27 (IgG2a) (Chemicon, Temecula Calif.) and the mouse IgG2a antibody (clone G155-178 from BD Biosciences; Oakville ON) to trinitrophenol, an irrelevant molecule, which was used as a negative IgG2a isotype control. 11BD-2E11-2 immunoprecipitate, IgG1 isotype control (clone 107.3) immunoprecipitate, anti-MCSP (clone 9.2.27) immunoprecipitate, IgG2a isotype control (clone G155-228) immunoprecipitate and MB-231 membranes were separated by SDS-PAGE on six replicate 10 percent gels. Electrophoresis and Western blotting were carried out as described above. The membranes were incubated with 5 µg/mL of 11BD-2E11-2, IgG1 isotype control (clone 107.3), anti-MCSP (clone 9.2.27), IgG2a isotype control (clone G155-228), rabbit polyclonal anti-rat NG2 antibody (MCSP is the human homologue of rat NG2; Chemicon, Temecula Calif.) and normal rabbit IgG (Sigma, Saint Louis Mo.) diluted in 3 percent skim milk powder in TBST for 2.5 hr. FIG. 4 demonstrates the results of the Western blotting as described. FIG. 4 (Panel A) shows the binding of 11BD-2E11-2 to 11BD-2E11-2 immunoprecipitate (Lane 1), IgG1 isotype control (clone 107.3) immunoprecipitate (Lane 2), anti-MCSP (clone 9.2.27) immunoprecipitate (Lane 3), IgG2a isotype control (clone G1155-228) immunoprecipitate (Lane 4), MB-231 membranes (Lane 5) and sample buffer only (negative control) (Lane 6). 11BD-2E11-2 recognized the same three bands of approximately 150, 240 and 280 kDa in both the MB-231 membranes and in the 11BD-2E11-2 immunoprecipitate. Only the upper 280 kDa band was recognized in the anti-MCSP (clone 9.2.27) immunoprecipitate lane. There is no reaction in either of the isotype control immunoprecipitate lanes, indicating that the reactivity of 11BD-2E11-2 to the immunoprecipitates was due to proteins being specifically bound and immunoprecipitated by both 11BD-2E11-2 and 9.2.27. In a parallel blot (Panel B) probed with IgG1 isotype control (clone 107.3), no reactivity was observed in any of the lanes, indicating that the reactivity observed in the blot probed with 11BD-2E11-2 was specific. Panel C shows the binding of rabbit polyclonal anti-rat NG2 antibody to a parallel blot. Anti-NG2 binds to two bands of approximately 150 and 240 kDa in the 11BD-2E11-2 immunoprecipitate (Lane 1) while it does not bind to proteins of this molecular weight range in any of the other lanes. In a parallel blot (Panel D), normal rabbit IgG shows faint non-specific reactivity to proteins in both the IgG2a immunoprecipitate (Lane 4) and MB-231 membranes (Lane 5). Therefore the same reactivity in these lanes on Panel C (probed with rabbit anti-NG2) should be regarded as non-specific. In a parallel blot (Panel E) anti-MCSP (clone 9.2.27) shows only very faint binding to one band in the anti-MCSP (clone 9.2.27) immunoprecipitate lane (Lane 3, indicated by arrow); this band is not seen in the MB-231 membranes (Lane 5) which indicates that 9.2.27 may have a low affinity for this antigen and only show reactivity when it is present in a concentrated form such as it is in the immunoprecipitated sample. In the final parallel blot (Panel F) probed with IgG2a isotype control (clone G155-228), no reactivity was observed in any of the lanes, indicating that the reactivity observed in the blot probed with anti-MCSP (clone 9.2.27) was specific. These results demonstrate that 11BD-2E11-2 immunoprecipitated protein was recognized by the rat homologue of MCSP, and that anti-MCSP immunoprecipitated protein was recognized by 11BD-2E11-2. The mass spectroscopic identification combined with the confirmation using known commercial antibodies demonstrates that the antigen for 11BD-2E11-2 is MCSP. This is also consistent with the deglycosylation experiments in Example 2, as the core protein of MCSP is a glycoprotein.

EXAMPLE 4

As outlined in Ser. No. 10/743,451, the hybridoma cell line 11BD-2E11-2 was deposited, in accordance with the Budapest Treaty, with the American Type Culture Collection, 10801 University Blvd., Manassas, Va. 20110-2209 on Nov. 11, 2003, under Accession Number PTA-5643. In accordance with CFR 1.808, the depositors assure that all restrictions imposed on the availability to the public of the deposited materials will be irrevocably removed upon the granting of a patent.

Antibody Production:

11BD-2E11-2 monoclonal antibody was produced by culturing the hybridoma in CL-1000 flasks (BD Biosciences, Oakville, ON) with collections and reseeding occurring twice/week. The antibody was purified according to standard antibody purification procedures with Protein G Sepharose 4 Fast Flow (Amersham Biosciences, Baie d'Urfé, QC).

As previously described in Ser. No. 10/348,231, 11BD-2E11-2 was compared to a number of both positive (anti-Fas (EOS9.1, IgM, kappa, 20 micrograms/mL, eBioscience, San Diego, Calif.), anti-Her2/neu (IgG 1, kappa, 10 microgram/mL, Inter Medico, Markham, ON), anti-EGFR(C225, IgG1, kappa, 5 microgram/mL, Cedarlane, Homby, ON), Cycloheximide (100 micromolar, Sigma, Oakville, ON), $NaN_3$ (0.1%, Sigma, Oakville, ON)) and negative (107.3 (anti-TNP, IgG1, kappa, 20 microgram/mL, BD Biosciences, Oakville, ON), G155-178 (anti-TNP, IgG2a, kappa, 20 microgram/mL, BD Biosciences, Oakville, ON), MPC-11 (antigenic specificity unknown, IgG2b, kappa, 20 microgram/mL), J606 (anti-fructosan, IgG3, kappa, 20 microgram/mL), IgG Buffer (2%)) controls in a cytotoxicity assay (Table 2). Breast cancer (MDA-MB-231 (MB-231), MDA-MB-468 (MB-468), MCF-7), colon cancer (HT-29, SW1116, SW620), lung cancer (NCI H460), ovarian cancer (OVCAR-3 (OVCAR)), prostate cancer (PC-3), and non-cancer (CCD 27sk, Hs888 Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, purified antibody or controls were diluted into media, and then 100 microliters were transferred to the cell plates and incubated in a 5 percent $CO_2$ incubator for 5 days. The plate was then emptied by inverting and blotted dry. Room temperature DPBS containing $MgCl_2$ and $CaCl_2$ was dispensed into each well from a multi-channel squeeze bottle, tapped three times, emptied by inversion and then blotted dry. 50 microliters of the fluorescent calcein dye diluted in DPBS containing $MgCl_2$ and $CaCl_2$ was added to each well and incubated at 37° C. in a 5 percent $CO_2$ incubator for 30 minutes. The plates were read in a Perkin-Elmer HTS7000 fluorescence plate reader and the data was analyzed in Microsoft Excel and the results were tabulated in Table 1. The data represented an average of four experiments tested in triplicate and presented qualitatively in the following fashion: 4/4 experiments greater than threshold cytotoxicity (+++), 3/4 experiments greater than threshold cytotoxicity (++), 2/4 experiments greater than threshold cytotoxicity (+). Unmarked cells in Table 1 represent inconsistent or effects less than the threshold cytotoxicity. 11BD-2E11-2 was specifically cytotoxic in breast and ovarian cancer cells, and did not affect normal cells. The chemical cytotoxic agents induced their expected cytotoxicity while a number of other antibodies which were included for comparison also performed as expected given the limitations of biological cell assays. In toto, it was shown that the 11BD-2E11-2 antibody has cytotoxic activity against two cancer cell types. The antibody was selective in its activity since not all cancer cell types were susceptible. Furthermore, the antibody demonstrated functional specificity since it did not produce cytotoxicity against non-cancer cell types, which is an important factor in a therapeutic situation.

TABLE 2

| | | BREAST | | | COLON | | | LUNG | OVARY | PROSTATE | NORMAL | |
|---|---|---|---|---|---|---|---|---|---|---|---|---|
| | | MB-231 | MB-468 | MCF-7 | HT-29 | SW1116 | SW620 | NCI H460 | OVCAR | PC-3 | CCD 27sk | Hs88 Lu |
| | 11BD2E11-2 | − | − | + | − | − | − | − | + | − | − | − |
| Positive | anti-Fas | − | − | +++ | − | − | − | − | +++ | + | − | + |
| Controls | anti-Her2 | + | − | + | − | − | − | − | + | − | − | − |
| | anti-EGFR | − | +++ | + | − | +++ | − | − | + | − | + | − |
| | CHX (100 μM) | +++ | +++ | +++ | +++ | +++ | +++ | +++ | +++ | +++ | +++ | +++ |
| | NaN$_3$ (0.1%) | +++ | +++ | +++ | +++ | − | − | +++ | +++ | +++ | − | − |
| Negative | IgG1 | | | | | | | | +++ | + | | |
| Controls | IgG2a | | | +++ | | + | | | | | | |
| | IgG2b | | | +++ | | | | | | | | |
| | IgG3 | | | | | | | | | | | |
| | IgG Buffer | + | | | | | | | | | | |

Binding of 11BD-2E11-2 to the above-mentioned panel of cancer and normal cell lines plus the following additional ovarian cancer cell lines (A2780-cp, A2780-s, C-14, OV2008, Hey, OCC-1, OVCA-429 and ES-2+SEAP) was assessed by flow cytometry (FACS). Cells were prepared for FACS by initially washing the cell monolayer with DPBS (without Ca$^{++}$ and Mg$^{++}$). Cell dissociation buffer (INVITROGEN, Burlington, ON) was then used to dislodge the cells from their cell culture plates at 37° C. After centrifugation and collection the cells were resuspended in Dulbecco's phosphate buffered saline containing MgCl$_2$, CaCl$_2$ and 2 or 25 percent fetal bovine serum (FBS) at 4° C. (wash media) and counted, aliquoted to appropriate cell density, spun down to pellet the cells and resuspended in staining media (DPBS containing MgCl$_2$ and CaCl$_2$ +/−2 percent FBS) containing 11BD-2E11-2 or control antibodies (isotype control or anti-EGFR) at 20 μg/mL on ice for 30 min. Prior to the addition of Alexa Fluor 488-conjugated secondary antibody the cells were washed once with wash media. The Alexa Fluor 488-conjugated antibody in staining media was then added for 20 to 30 min. The cells were then washed for the final time and resuspended in staining media containing 1 μg/mL propidium iodide or 1.5 percent paraformaldehyde. Flow cytometric acquisition of the cells was assessed by running samples on a FACScan using the CellQuest software (BD Biosciences, Oakville, ON). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform peak with a median fluorescent intensity of approximately 1-5 units. Live cells were acquired by gating for FSC and propidium iodide exclusion (when used). For each sample, approximately 10,000 live cells were acquired for analysis and the resulted presented in Table 3 and 4. Tables 3 and 4 tabulated the mean fluorescence intensity fold increase above isotype control and is presented qualitatively as: less than 5 (−); 5 to 50 (+); 50 to 100 (++); above 100 (+++) and in parenthesis, the percentage of cells stained.

Figure 5:
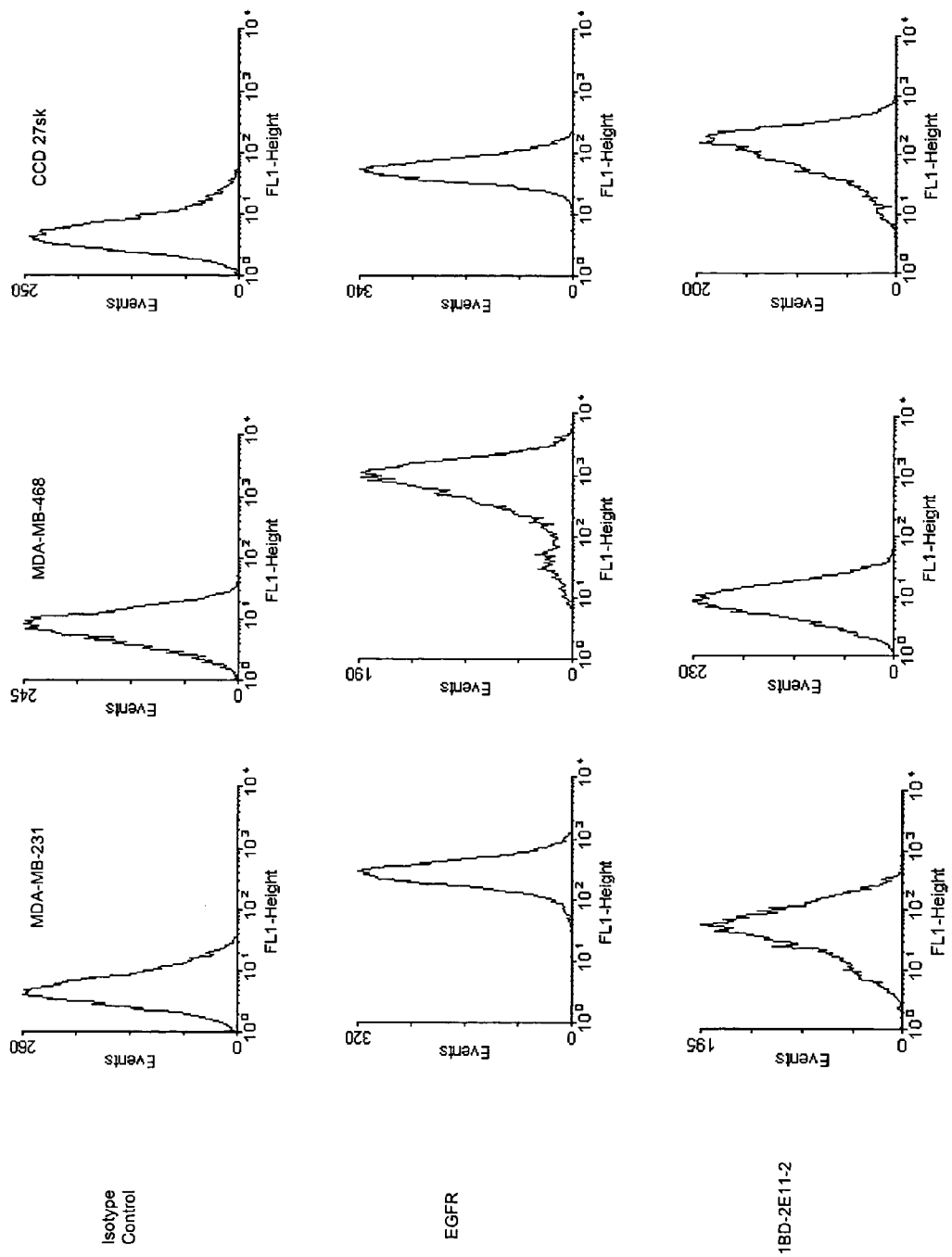
FIG. 5. Representative FACS histograms of 11BD-2E11-2, isotype control or anti-EGFR directed against several cancer cell lines and non-cancer cells.

Representative histograms of 11BD-2E11-2 antibodies were compiled for FIG. 5. 11BD-2E11-2 displayed specific tumor binding to the breast tumor cell line MDA-MB-231 (Table 3) and several ovarian tumor cell lines including ES-2+SEAP (Table 4). There was also binding of 11BD-2E11-2 to non-cancer cells, however that binding did not produce cytotoxicity. This was further evidence that binding was not necessarily predictive of the outcome of antibody ligation of its cognate antigen, and was a non-obvious finding. This suggested that the context of antibody ligation in different cells was determinative of cytoxicity rather than just antibody binding.

TABLE 3

| | | BREAST | | | COLON | | | LUNG | OVARY | PROSTATE | NORMAL | | |
|---|---|---|---|---|---|---|---|---|---|---|---|---|---|
| Antibody | Isotype | MB-231 | MB-468 | MCF-7 | HT-29 | SW1116 | SW620 | NCI H460 | OVCAR | PC-3 | CCD 27sk | CCD-112 | Hs888 Lu |
| 11BD-2E11-2 | IgG1, k | + | − | − | − | − | − | − | − | − | + | + | + |
| anti-EGFR | IgG1, k | ++ | ++ | − | + | + | − | + | + | + | + | + | + |

TABLE 4

| | | Ovarian | | | | | | | |
|---|---|---|---|---|---|---|---|---|---|
| Antibody | Isotype | A2780-cp | A2780-s | C-14 | OV2008 | ES-2 + SEAP | Hey | OCC-1 | OVCA-429 |
| 11BD-2E11-2 | IgG1, k | + | + | − | − | + | + | + | − |
| anti-EGFR | IgG1, k | − | − | + | + | + | + | + | + |

EXAMPLE 5

Normal Human Tissue Staining

IHC studies were conducted to characterize 11BD-2E11-2 antigen distribution in humans. IHC optimization studies were performed previously in order to determine the conditions for further experiments. 11BD-2E11-2 monoclonal antibody was produced and purified as stated above.

Binding of antibodies to 20 normal human tissues was performed using a frozen human normal organ tissue array (Clinomics, Wateryliet, N.Y.). Slides were postfixed for 10 min in cold (−20° C.) acetone and then allowed to come to room temperature. Slides were rinsed in 4° C. cold phosphate buffered saline (PBS) 3 times for 2 min each followed by blocking endogenous peroxidase activity with washing in 3 percent hydrogen peroxide for 10 min. Slides were then rinsed in PBS 3 times for 5 min followed by incubation in Universal blocking solution (Dako, Toronto, Ontario) for 5 min at room temperature. 11BD-2E11-2, anti-human muscle actin (Clone HHF35, Dako, Toronto, Ontario) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 µg/mL for each antibody except for anti-actin which was 2 µg/mL) and incubated overnight for 1 hr at room temperature. The slides were washed with PBS 3 times for 2 minutes each. Immunoreactivity of the primary antibodies was detected/visualized with HRP conjugated secondary antibodies as supplied (Dako Envision System, Toronto, Ontario) for 30 min at room temperature. Following this step the slides were washed with PBS 3 times for 2 min each and a color reaction developed by adding DAB (3,3'-diaminobenzidine tetrahydrachloride, Dako, Toronto, Ontario) chromogen substrate solution for immunoperoxidase staining for 10 min at room temperature. Washing the slides in tap water terminated the chromogenic reaction. Following counterstaining with Meyer's Hematoxylin (Sigrna Diagnostics, Oakville, ON), the slides were dehyrdated with graded ethanols (95-100%) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a pathologist.

Figure 6:
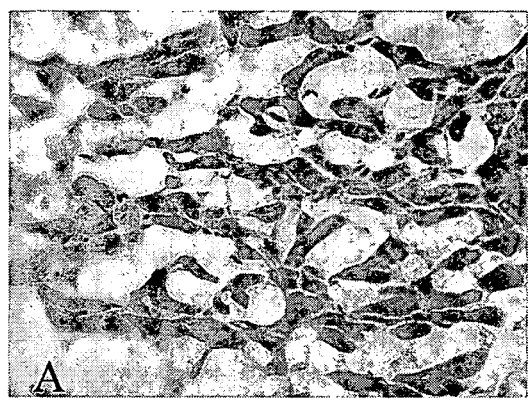
FIG. 6. Representative micrographs showing the binding pattern obtained with 11BD-2E11-2 (A) and the isotype control antibody (B) on tissues sections of heart from a frozen normal human tissue array. There is no staining of 11BD-2E11-2 to cardiac muscle fibers. Magnification is 200×.
Figure 6:
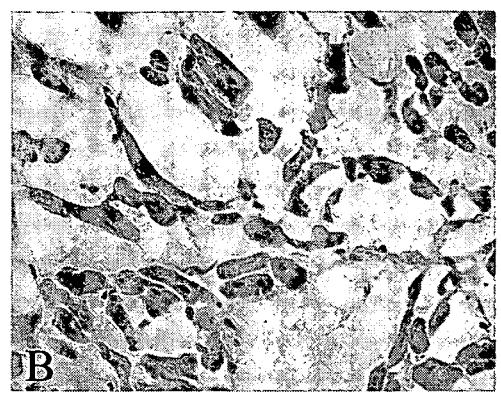
Figure 7:
FIG. 7. Representative micrographs showing the binding pattern obtained with 11BD-2E11-2 (A), anti-actin (B) and the isotype control antibody (C) on tissues sections of skeletal muscle from a frozen normal human tissue array. 11BD-2E11-2 did not stain skeletal muscle but there is staining to the smooth muscles of blood vessels (arrow). Magnification is 200×.
Figure 7:
Figure 7:
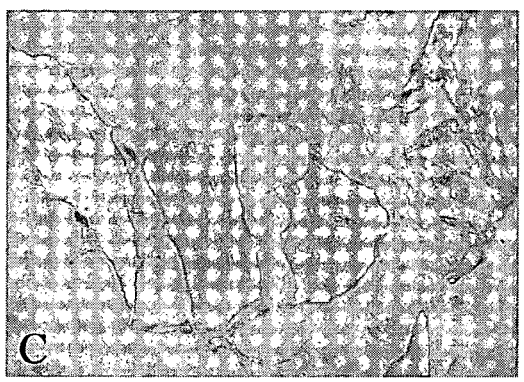

Table 5 presents a summary of the results of 11BD-2E11-2 staining of an array of normal human tissues. From the table, there were 2 main categories of tissue staining. A group of tissues was completely negative. These tissues included normal thyroid, bronchus and cardiac muscle of the left ventricle (FIG. 6). The second group of tissues included tissues in which staining was positive in the tissue section, but was limited to smooth muscle fibers of blood vessels and/or the epithelium (FIG. 7). These results suggested that the antigen for 11BD-2E11-2 was not widely expressed on normal tissues, and that the antibody would bind only to a limited number of tissues in humans. The normal human tissue staining of 11BD-2E11-2 resembles that previously reported for an anti-MCSP antibody; B5. B5 was previously shown to bind to skin keratinocytes, lung alveolar epithelium and capillary endothelium.

TABLE 5

11BD-2E11-2 IHC on Frozen Human Normal Tissue

| 1 | Bronchus | 61 | M | − (PD) | +++ SMF & Myoepithelium of mucus acini | CD |
|---|---|---|---|---|---|---|
| 2 | Diaphragm | 61 | M | +++ SMF of blood vessels +/− Skeletal muscle fibers | +++ Skeletal muscle fibers & SMF of blood vessels | — |
| 3 | Pectoral muscle (Skeletal muscle) | 61 | M | +++ SMF of blood vessels | +++ Skeletal muscle fibers & SMF of blood vessels | — |
| 4 | Lung | 61 | M | +++ Alveolar epithelium & SMF of blood vessels | CD | − (F) |
| 5 | Aorta | 61 | M | ++ SMF (F) | CD | — |
| 6 | Left ventricle (Cardiac muscle) | 61 | M | — | +++ SMF of blood vessels + Cardiac muscle fibers | — |
| 7 | Esophagus | 61 | M | +++ SMF (PD) | CD | − (F) |
| 8 | Trachea | 61 | M | − (PD) | +++ SMF & myoepithelium of mucus acini | — |
| 9 | Kidney | 61 | M | +++ SMF of blood vessels | +++ SMF of blood vessels | — |
| 10 | Adrenal | 61 | M | +++ SMF of blood vessels | +++ SMF of blood vessels | — |
| 11 | Pancreas | 61 | M | +++ SMF of blood vessels + Acinar epithelium | +++ SMF of blood vessels | — |
| 12 | Spleen | 61 | M | +++ SMF of blood vessels & Polymorphs (F) | +++ SMF of blood vessels, reticular fibers & polymorphs (F) | Bg (polymorphs) |
| 13 | Liver | 61 | M | +++ SMF of blood vessels | − (PD) | — |
| 14 | Skin | 61 | M | +++ SMF of blood vessels +/− Keratinocytes | +++ SMF of blood vessels | Bg (Stroma) |
| 15 | Colon | 61 | M | +++ SMF of blood vessels | +++ SMF | — |
| 16 | Thyroid | 61 | M | − (PD) | − (PD) | — |
| 17 | Prostate | 61 | M | ++ SMF of blood vessels +/− Glandular epithelium | CD | CD |
| 18 | Testicle | 61 | M | ++ SMF of blood vessels | +++ stromal cells | — |
| 19 | Breast | 61 | M | +/− Ductal epithelium +++ SMF of blood vessels | +++ SMF of blood vessels | — |
| 20 | Ovary | 80 | F | ++ SMF of blood vessels & Stroma | F | CD |

Abbreviations:
SMF: smooth muscle fiber,
Bg: background staining,
PD: partially detached,
F: folded,
CD: completely detached.

EXAMPLE 6

Human Breast Tumor Tissue Staining

An IHC study was undertaken to determine the cancer association of the 11BD-2E11-2 antigen with human breast cancers. A comparison was made for actin (positive control), and an antibody directed towards *Aspergillus niger* glucose oxidase, an enzyme which is neither present nor inducible in mammalian tissues (negative control). A breast cancer tissue array derived from 15 breast cancer patients and 5 samples derived from non-neoplastic breast tissue in breast cancer patients were used (Clinomics, Watervliet, N.Y.). The following information was provided for each patient: age, sex, and diagnosis. The procedure for IHC from Example 5 was followed.

Figure 8:
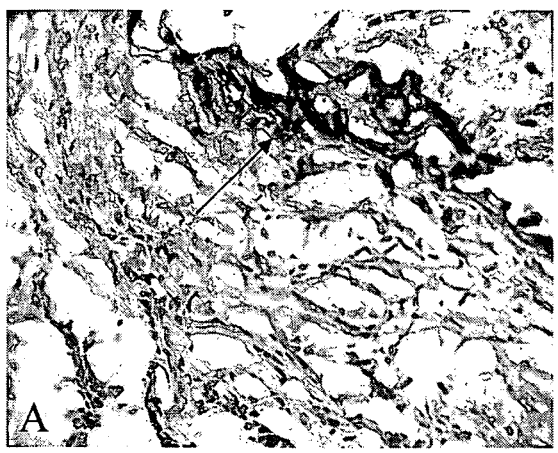
FIG. 8. Representative micrograph of 11BD-2E11-2 (A) and isotype control antibody (B) binding to breast cancer tumor (infiltrating duct carcinoma). The black arrow in panel A points to tumor cells. Magnification is 200×.
Figure 8:
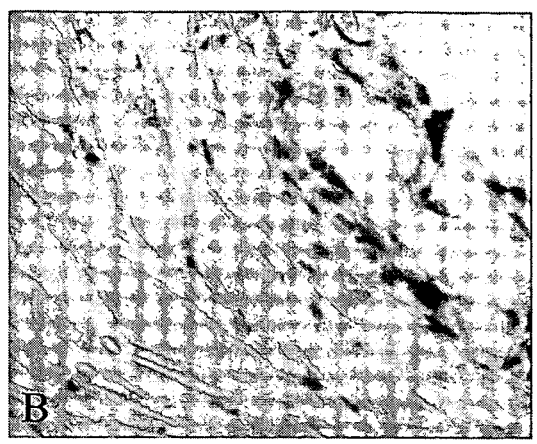

Table 6 provides a binding summary of 11BD-2E11-2 antibody staining of a breast cancer tissue array. Each array contained tumor samples from 15 individual patients. Overall, 62 percent of the 8 (7 of the tissue samples were either completely detached or not representative) patients tested were positive for the 11BD-2E11-2 antigen. Also for 11BD-2E11-2, 0 out of 3 (again 2 of the tissue samples were completely detached) normal breast tissue samples from breast cancer patients were positive (FIG. 8). For the 11BD-2E11-2 antigen there did not appear to be a trend to greater positive expression with higher tumor stage. However, this result was limited due to the small sample size. The 11BD-2E11-2 staining was specific for cancerous cells (FIG. 8). The staining pattern, from 11BD-2E11-2, showed that in patient samples, the antibody was highly specific for malignant cells thereby making it an attractive druggable target. The breast tumor tissue staining of 11BD-2E11-2 resembles that previously reported for the anti-MCSP antibody B5. B5 was previously shown to bind to 60 percent of breast carcinoma tumor tissue.

TABLE 6

11BD-2E11-2 IHC on Frozen Human Normal and Breast Tumor Tissue

Data Sheet

| | | | | | IHC Score | | |
|---|---|---|---|---|---|---|---|
| S. NO. | Tissue | Age | Sex | Diagnosis | 11BD-2E11-2 | Actin | IgG negative control |
| 1 | Breast | 61 | F | Infiltrating Ductal Carcinoma | CD | CD | CD |
| 2 | Breast | 74 | F | Infiltrating Ductal Carcinoma | – (PD) | – Tumor +++ SMF of blood vessels | — |
| 3 | Breast | 60 | F | Infiltrating Ductal Carcinoma | CD | PD | CD |
| 4 | Breast | 69 | F | Infiltrating Ductal Carcinoma | NR | NR | — |
| 5 | Breast | 64 | F | Infiltrating Ductal Carcinoma | CD | — | CD |
| 6 | Breast | 65 | F | Medullary Carcinoma | +++ (Tumor cells) | — | — |
| 7 | Breast | 75 | F | Infiltrating Ductal Carcinoma | +++ (Tumor cells) | CD | — |
| 8 | Breast | 48 | F | Infiltrating Ductal Carcinoma | ++ (Tumor cells) | – Tumor ++ Stroma | — |
| 9 | Breast | 87 | F | Infiltrating Ductal Carcinoma | +/– (Tumor cells) | – Tumor +++– SMF of blood vessels | CD |
| 10 | Breast | 75 | F | Infiltrating Ductal Carcinoma | NR (+/– SMF of blood vessels) | CD | — |
| 11 | Breast | 76 | F | Infiltrating Ductal Carcinoma | — | – Tumor +++ SMF of blood vessels & stroma | — |
| 12 | Breast | 66 | F | Infiltrating Ductal Carcinoma | CD | CD | — |
| 13 | Breast | 58 | F | Infiltrating Ductal Carcinoma | +++ (Tumor cells) | CD | CD |
| 14 | Breast | 37 | F | Infiltrating Ductal Carcinoma | CD | – Tumor +++ Stroma | — |
| 15 | Breast | 70 | F | Infiltrating Ductal Carcinoma | — | – Tumor +++ Myoepithelium & SMF of blood vessels | CD |
| 16 | Breast | 48 | F | Normal | – (PD) | CD | CD |
| 17 | Breast | 60 | F | Normal | — | – (PD) | — |
| 18 | Breast | 30 | F | Normal | CD | – Tumor +++ Myoepithelium & SMF of blood vessels | — |
| 19 | Breast | 34 | F | Normal | CD | – Tumor ++ Myoepithelium (PD) | — |
| 20 | Breast | 43 | F | Normal | — | – Tumor + SMF of blood vessels | — |

Abbreviations:

SMF: smooth muscle fiber,

PD: partially detached,

F: folded,

CD: completely detached.

EXAMPLE 7

In Vivo MDA-MB-468 Established Tumor Experiment

With reference to FIG. 9, 6 to 8 week old female SCID mice were implanted with 2 million MDA-MB-468 human breast cancer cells in 100 microlitres saline injected subcutaneously in the scruff of the neck. Tumor growth was measured with calipers every week. When the majority of the cohort reached a tumor volume of 100 mm$^3$, 5-6 mice were randomized into each of 2 treatment groups. 11BD-2E11-2 or buffer control was administered intraperitoneally with 10 mg/kg/dose at a volume of 300 microliters after dilution from the stock concentration with a diluent that contained 2.7 mM KCl, 1 mM KH$_2$PO$_4$ 137 mM NaCl and 20 mM Na$_2$HPO$_4$. The antibodies were then administered 3 times per week for a total of 10 doses in the same fashion until day 66 post-implantation. Tumor growth was measured about every seventh day with calipers for the duration of the study or until individual animals reached CCAC end-points. Body weights of the animals were recorded for the duration of the study. At the end of the study all animals were euthanised according to CCAC guidelines.

Figure 9:
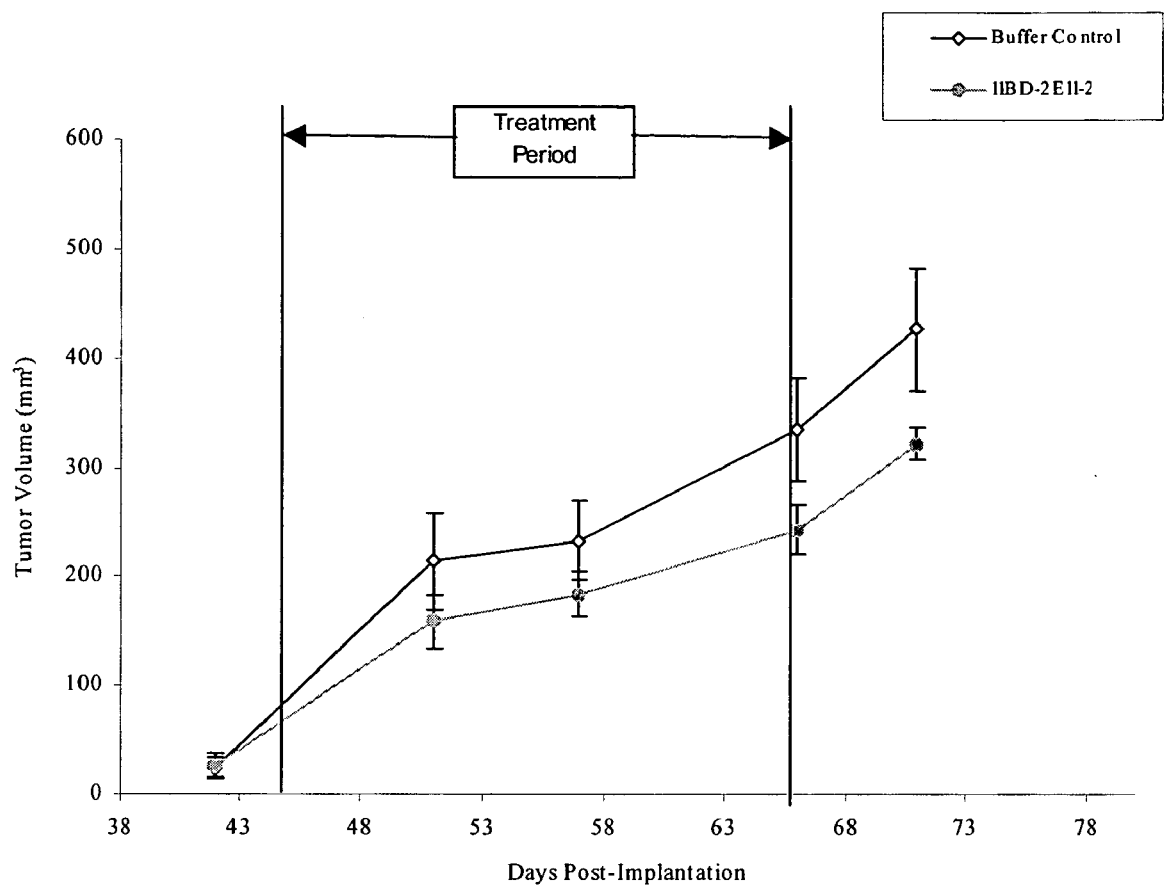
FIG. 9. Effect of 11BD-2E11-2 or buffer control on tumor growth in a preventative MDA-MB-468 breast cancer model. The dashed line indicates the period during which the antibody was administered. Data points represent the mean+/− SEM.

At the time of randomization the mean tumor volumes and the standard deviations in each group were similar. Statistically there was no difference in body weight between the groups. This indicated that true randomization had occurred. As shown in FIG. 9, the antibody 11BD-2E11-2 suppressed tumor growth by 25 percent in comparison to buffer control at the end of the 3-week treatment period ($p=0.52$). Although this was not a significant difference, a trend towards reduced tumor volume in comparison to the buffer control was observed throughout the study. Therefore, 11BD-2E11-2 has shown efficacy in an established breast cancer model.

EXAMPLE 8

In Vivo ES-2+SEAP Established Tumor Experiment

With reference to FIGS. 10 and 11, 6 to 8 week old female athymic nude mice were intraperitoneally implanted with 10 million ES-2+SEAP human ovarian cancer cells stably transfected to express human placental secreted alkaline phosphatase (SEAP). The 10 million ovarian cancer cells were resuspended in 500 microlitres serum-free α-MEM. Tumor growth was confirmed with the sacrifice of 3 mice on day 7. Following the confirmation of tumor growth on day 7, 8 mice were randomized into each of 2 treatment groups. 11BD-2E11-2 or buffer control was administered intraperitoneally with 10 mg/kg/dose at a volume of 250 microliters after dilution from the stock concentration with a diluent that contained 2.7 mM KCl, 1 mM KH$_2$PO$_4$, 137 mM NaCl and 20 mM Na$_2$HPO$_4$. The antibodies were then administered once per day for 5 doses and then once every other day for another 5 doses for a total of 10 doses. Tumor burden was extrapolated by measuring circulating SEAP levels and assessed visually upon necropsy for the duration of the study or until individual animals reached CCAC end-points. Body weights of the animals were recorded for the duration of the study. At the end of the study all animals were euthanised according to CCAC guidelines.

Figure 10:
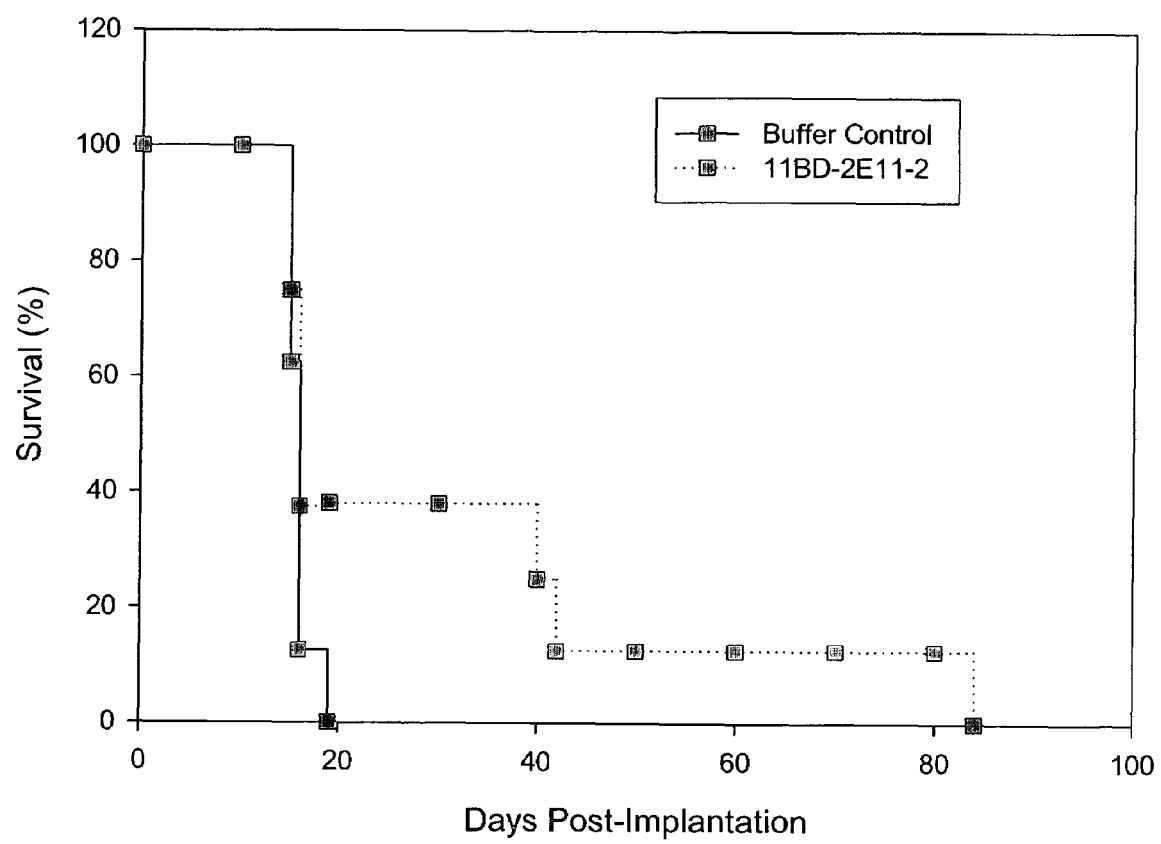
FIG. 10. Survival of tumor-bearing mice after treatment with 11BD-2E11-2 or buffer control antibody in an established ES-2 xenograft study.
Figure 11:
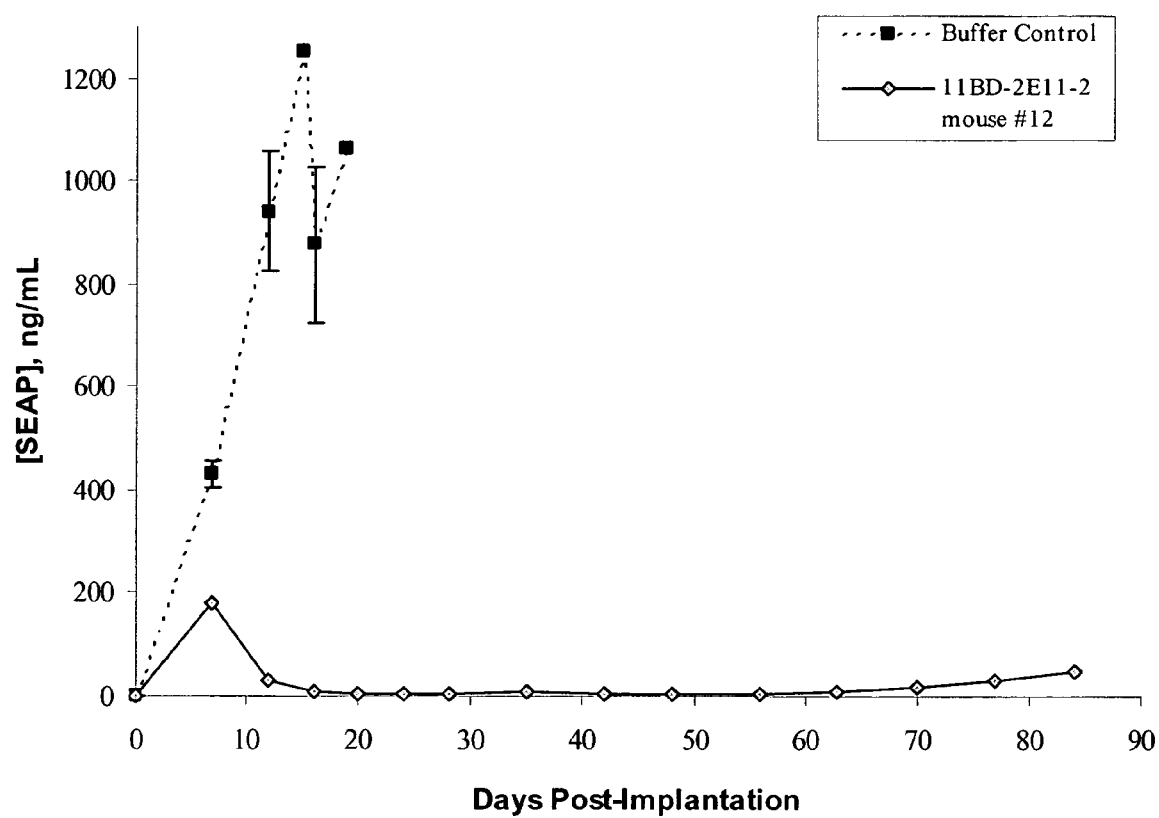
FIG. 11. SEAP levels of tumor-bearing mice before, during and after treatment with 11BD-2E11-2 or buffer control in an established ES-2 xenograft study.

At the time of randomization circulating plasma SEAP levels (indicative of tumor burden) were analyzed. There was not a significant difference in the average SEAP level between the 11BD-2E11-2 and buffer control treatment group. However, within groups there was variable tumor take-rate. As shown in FIG. 10, the antibody 11BD-2E11-2 displayed a trend for improved survival in a cohort of the treatment group. As illustrated in FIG. 11, one animal receiving 11BD-2E11-2 treatment had a decreased amount of circulating SEAP to nearly negligible levels. The low level of circulating SEAP continued on until approximately 60 days post-implantation. In all, these results in which 11BD-2E11-2 produced benefits (improved survival and decreased tumor burden in comparison to control treatment) in mulitple models of human cancer suggest pharmacologic and pharmaceutical benefits of this antibody for cancer therapy in mammals, including man.

The preponderance of evidence shows that 11BD-2E11-2 mediates anti-cancer effects through ligation of an epitope present on MSCP. For the purpose of this invention, said epitope is defined as a "MSCP antigenic moiety" characterized by its ability to bind with a monoclonal antibody encoded by the hybridoma cell line 11BD-2E11-2, antigenic binding fragments thereof or antibody conjugates thereof. It has been shown, in Example 3, 11BD-2E11-2 antibody can be used to immunoprecipitate the cognate antigen from expressing cells such as MDA-MB-231 cells. Further it could be shown that the 11BD-2E11-2 antibody could be used in detection of cells and/or tissues which express a MSCP antigenic moiety which specifically binds thereto, utilizing techniques illustrated by, but not limited to FACS, cell ELISA or IHC.

Thus, it could be shown that the immunoprecipitated 11BD-2E11-2 antigen can inhibit the binding of 11BD-2E11-2 to such cells or tissues using FACS, cell ELISA or IHC assays. Further, as with the 11BD-2E11-2 antibody, other anti-MSCP antibodies could be used to immunoprecipitate and isolate other forms of the MSCP antigen, and the antigen can also be used to inhibit the binding of those antibodies to the cells or tissues that express the antigen using the same types of assays.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for treating a patient suffering from a breast or ovarian cancerous disease comprising:

administering to said patient an isolated monoclonal antibody or antigen binding fragment thereof produced in accordance with a method for the production of anti-cancer antibodies which are useful in treating said breast or ovarian cancerous disease, said isolated monoclonal antibody or antigen binding fragment thereof characterized as being cytotoxic against cells of said cancerous tissue;

wherein said isolated monoclonal antibody or antigen binding fragment thereof is placed in admixture with a pharmaceutically acceptable adjuvant and is administered in an amount effective to mediate treatment of said cancerous disease;

said antibody being an isolated monoclonal antibody or antigen binding fragment thereof which binds to the same epitope which is bound by the isolated monoclonal antibody produced by a hybridoma deposited with the ATCC as PTA-5643.

2. The method for treating a patient suffering from said cancerous disease in accordance with claim 1, wherein said isolated monoclonal antibody is a humanized antibody of the isolated monoclonal antibody produced by the hybridoma deposited with the ATCC under accession number PTA-5643.

3. The method for treating a patient suffering from said cancerous disease in accordance with claim 1 comprising:

conjugating said isolated monoclonal antibody or antigen binding fragment thereof with a member selected from the group consisting of toxins, radioactive compounds, and hematogenous cells, thereby forming an antibody conjugate; and administering said antibody conjugate or conjugated antigen binding fragments to said patient;

wherein said antibody conjugate or conjugated fragments are placed in admixture with a pharmaceutically acceptable adjuvant and are administered in an amount effective to mediate treatment of said cancerous disease.

4. The method of claim 3, wherein said isolated monoclonal antibody is a humanized antibody of the isolated monoclonal antibody produced by the hybridoma deposited with the ATCC under accession number PTA-5643.

5. The method for treating a patient suffering from a cangerous disease in accordance with claim 1 wherein:

said method of production is perfored with a tissue sample containing cancerous and non-cancerous cells obtained from said patient.

6. A method for treating a patient suffering from a breast or ovarian cancerous disease comprising:

administering to said patient an isolated monoclonal antibody or antigen binding fragment thereof produced in accordance with a method for the production of antibodies which are useful in treating said cancerous disease, said antibody being cytotoxic against cells of said cancerous tissue;

wherein said antibody is the isolated monoclonal antibody deposited with the ATCC as PTA-5643 or an antigen binding fragment thereof; and wherein said isolated monoclonal antibody or antigen binding fragment is placed in admixture with a pharmaceutically acceptable adjuvant and is administered in an amount effective to mediate treatment of said cancerous disease.

7. The method for treating a patient suffering from a cancerous disease in accordance with claim 6, wherein said isolated monoclonal antibody is a humanized antibody of the isolated monoclonal antibody produced by the hybridoma deposited with the ATCC under accession number PTA-5643.

8. The method for treating a patient suffering from a cancerous disease in accordance with claim 6 comprising:

conjugating said isolated monoclonal antibody or antigen binding fragment thereof with a member selected from the group consisting of toxins, radioactive compounds, and hematogenous cells, whereby an antibody conjugate is formed; and administering said antibody conjugates or antigen binding fragments thereof to said patient;

wherein said conjugated antibodies or antigen binding fragments thereof are placed in admixture with a pharmaceutically acceptable adjuvant and are administered in an amount effective to mediate treatment of said cancerous disease.

9. The method of claim 8, wherein said isolated monoclonal antibody is a humanized antibody of the isolated monoclonal antibody produced by the hybridoma deposited with the ATCC under accession number PTA-5643.

10. The method for treating a patient suffering from a cancerous disease in accordance with claim 6 wherein:

said method of production is performed with a tissue sample containing cancerous and noncancerous cells obtained from said patient.

* * * * *